US011864879B2

(12) United States Patent
Bien et al.

(10) Patent No.: US 11,864,879 B2
(45) Date of Patent: Jan. 9, 2024

(54) ANTENNA DEVICE FOR MEASURING BIOMETRIC INFORMATION BY USING MAGNETIC DIPOLE RESONANCE

(71) Applicant: UNIST (ULSAN NATIONAL INSTITUTE OF SCIENCE AND TECHNOLOGY), Ulsan (KR)

(72) Inventors: Franklin Don Bien, Ulsan (KR); Gang Il Byun, Ulsan (KR)

(73) Assignee: UNIST (ULSAN NATIONAL INSTITUTE OF SCIENCE AND TECHNOLOGY), Ulju-gun Ulsan (KR)

(*) Notice: Subject to any disclaimer, the term of this patent is extended or adjusted under 35 U.S.C. 154(b) by 234 days.

(21) Appl. No.: 17/526,980

(22) Filed: Nov. 15, 2021

(65) Prior Publication Data

US 2022/0071504 A1 Mar. 10, 2022

Related U.S. Application Data

(63) Continuation of application No. PCT/KR2020/008013, filed on Jun. 19, 2020.

(30) Foreign Application Priority Data

Jun. 21, 2019 (KR) .................. 10-2019-0074031
Jun. 17, 2020 (KR) .................. 10-2020-0073518

(51) Int. Cl.
*A61B 5/055* (2006.01)
*A61B 5/145* (2006.01)
(Continued)

(52) U.S. Cl.
CPC .............. *A61B 5/055* (2013.01); *A61B 5/145* (2013.01); *A61B 5/155* (2013.01); *G01N 24/08* (2013.01)

(58) Field of Classification Search
CPC ......... A61B 5/055; A61B 5/145; A61B 5/155; A61B 5/14532; A61B 5/242; G01N 24/08; H01Q 1/38; H01Q 1/273; H01Q 1/50
See application file for complete search history.

(56) References Cited

U.S. PATENT DOCUMENTS 9,387,331 B2 7/2016 Zhao et al.
2009/0281401 A1* 11/2009 Takenaka ............. A61B 1/0011
600/302
(Continued)

FOREIGN PATENT DOCUMENTS

EP 2 359 899 B1 8/2011
JP 2002246816 A 8/2002
(Continued)

OTHER PUBLICATIONS

International Search Report dated Sep. 22, 2020, issued in corresponding International Application No. PCT/KR2020/008013, filed Jun. 19, 2020, 2 pages.
(Continued)

*Primary Examiner* — G. M. A Hyder
(74) *Attorney, Agent, or Firm* — Christensen O'Connor Johnson Kindness PLLC

(57) ABSTRACT

An antenna device includes: a first and a second conductive wire; a third and a fourth conductive wire which are disposed along a part of the boundary of a second area on a second plane parallel to and spaced apart from the first plane while being spaced apart from each other; a fifth and a sixth conductive wire which are disposed along a part of the boundary of a third area on a third plane parallel to and spaced apart from the second plane while being spaced apart from each other; connection parts connecting the second conductive wires.

18 Claims, 21 Drawing Sheets

(51) Int. Cl.
    *A61B 5/155*    (2006.01)
    *G01N 24/08*    (2006.01)

(56) References Cited

U.S. PATENT DOCUMENTS

2011/0196462 A1    8/2011    Weiss et al.
2013/0200721 A1    8/2013    Kurs et al.

FOREIGN PATENT DOCUMENTS

| JP | 2015-508987 A | 3/2015 |
| KR | 10-2008-0075332 A | 8/2008 |
| KR | 10-0856507 B1 | 8/2008 |
| WO | 2018/051328 A1 | 3/2018 |

OTHER PUBLICATIONS

Written Opinion of the International Searching Authority dated Sep. 22, 2020, issued in corresponding International Application No. PCT/KR2020/008013, filed Jun. 19, 2020, 6 pages.

* cited by examiner

100

200

501

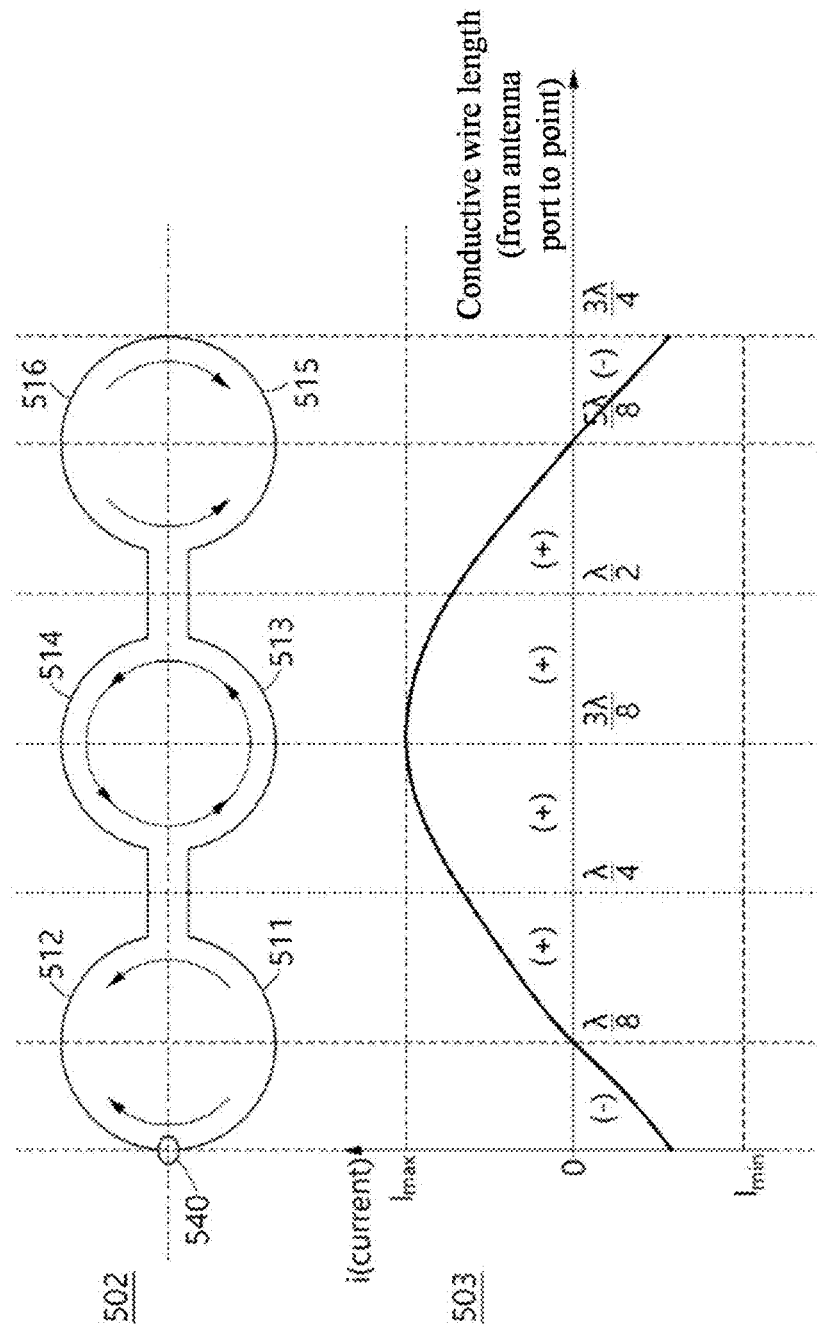

800

901

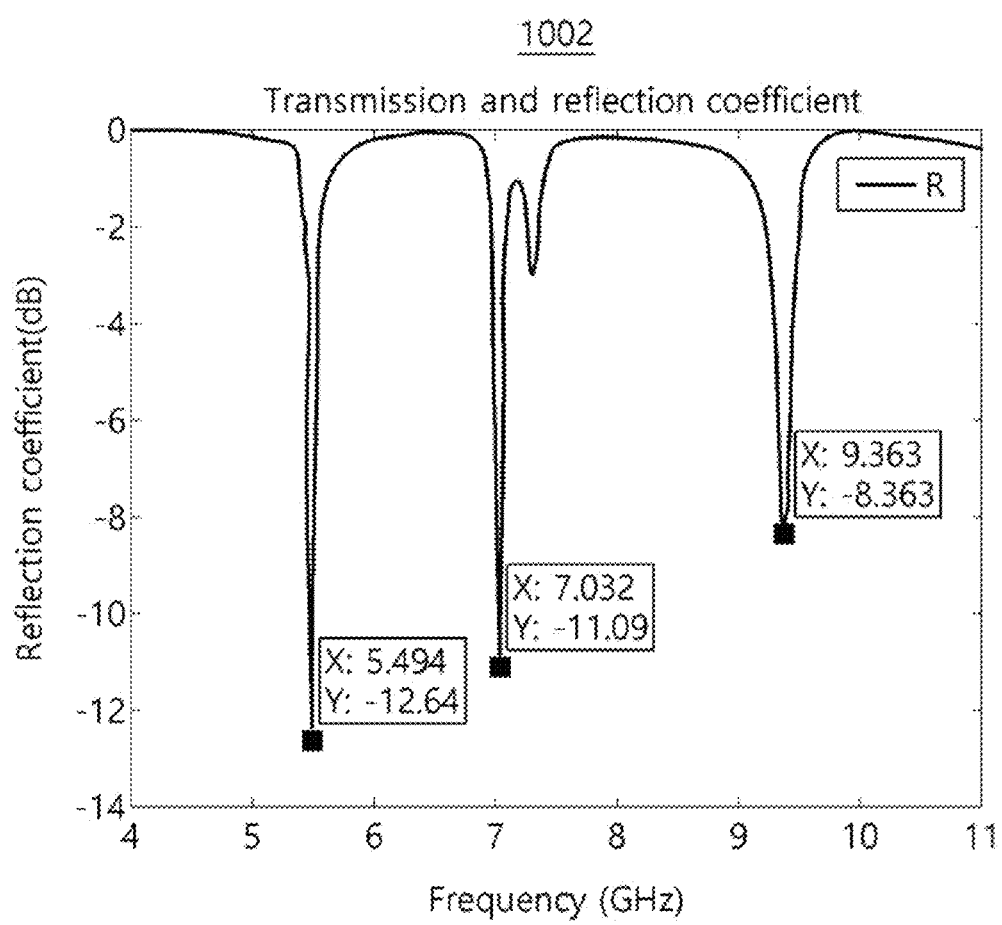

1003

1300

ANTENNA DEVICE FOR MEASURING BIOMETRIC INFORMATION BY USING MAGNETIC DIPOLE RESONANCE

CROSS-REFERENCES TO RELATED APPLICATIONS

This is a continuation of International Application No. PCT/KR2020/008013, filed Jun. 19, 2020, which claims the benefits of Korean Patent Application No. 10-2019-0074031, filed Jun. 21, 2019 and Korean Patent Application No. 10-2020-0073518, filed Jun. 17, 2020.

BACKGROUND OF INVENTION

Field of Invention

The present disclosure relates to an antenna device for measuring biometric information by using magnetic dipole resonance.

Description of Related Art

Recently, more and more people are suffering from so-called adult-onset diseases such as diabetes, hyper lipidemia, blood clots, etc., attributed to the westernization of dietary habits. A simple way of figuring out the seriousness of these diseases is to measure biological components in the blood. The measurement of biological components allows for detecting the amounts of various components in the blood associated with glucose, anemia, blood clots, etc., which is advantageous in that any one can find out whether the level of a particular component is in a normal range or in an abnormal range, without going to a clinic.

One of the simplest methods of biological component measurement is to inject a drop of blood drawn from a fingertip into a test strip and then perform quantitative analysis of an output signal by electrochemistry or photometry. This method is suitable for people with no expertise knowledge since the meter displays the amounts of components.

What follows is a technology that measures glucose levels in the body by inserting a glucose measurement sensor into the body and observing transitions in frequency, without directly extracting blood.

BRIEF SUMMARY OF THE INVENTION

An antenna device according to an embodiment may include: a first conductive wire and a second conductive wire which are disposed along a part of the boundary of a first area in a first plane while being spaced apart from each other; a third conductive wire and a fourth conductive wire which are disposed along a part of the boundary of a second area in a second plane parallel to and spaced apart from the first plane while being spaced apart from each other; a fifth conductive wire and a sixth conductive wire which are disposed along a part of the boundary of a third area in a third plane parallel to and spaced apart from the second plane while being spaced apart from each other; a first connection part connecting a first end of the first conductive wire to a first end of the third conductive wire; a second connection part connecting a first end of the second conductive wire to a first end of the fourth conductive wire; a third connection part connecting a second end of the third conductive wire to a second end of the fifth conductive wire; and a fourth connection part connecting a second end of the fourth conductive wire to a second end of the sixth conductive wire.

In the antenna device according to an embodiment, the second end of the first conductive wire and the second end of the second conductive wire are connected to an antenna port, the first conductive wire and the second conductive wire are disposed opposite each other with respect to a virtual plane passing through the antenna port and the center point of the first area and perpendicular to the first plane, the third conductive wire and the fourth conductive wire are disposed opposite each other with respect to the virtual plane, and the fifth conductive wire and the sixth conductive wire are disposed opposite each other with respect to the virtual plane.

The antenna device may further include: an antenna port to which the first conductive wire and the second conductive wire are connected; and a feeder for supplying a feed signal via the antenna port.

In the antenna device according to an embodiment, a combination of one or two of the first conductive wire, the second conductive wire, the third conductive wire, the fourth conductive wire, the fifth conductive wire, and the sixth conductive wire may have a length of ¼ of the wavelength of a target frequency.

In the antenna device according to an embodiment, the first area, the second area, and the third area may be either polygonal or circular.

In the antenna device according to an embodiment, the first area, the second area, and the third area may be equal in size and shape when viewed from a direction perpendicular to the first plane.

In the antenna device according to an embodiment, the first connection part and the second connection part may be disconnected from each other, and the third connection part and the fourth connection part may be disconnected from each other.

In the antenna device according to an embodiment, a virtual straight line from the feeder to the first connection part may be at a threshold angle or lower with respect to the virtual plane, and a virtual straight line from the feeder to the second connection part may be at a threshold angle or lower with respect to the virtual plane.

In the antenna device according to an embodiment, conductive wires disposed in a reference plane positioned halfway through a plurality of planes parallel to and spaced apart from each other may generate a resonance by a magnetic dipole, in response to a feed signal.

In the antenna device according to an embodiment, conductive wires disposed in one or more planes positioned on one side of the reference plane may generate a resonance by a first electric dipole in response to the feed signal, and conductive wires disposed in one or more planes positioned on the other side of the reference plane may generate a resonance by a second electric dipole of the opposite polarity to the first electric dipole in response to the feed signal.

In the antenna device according to an embodiment, the connection parts may connect between the conductive wires through via holes.

In the antenna device according to an embodiment, the fifth conductive wire and the sixth conductive wire may be electrically connected to each other.

The antenna device may further include one or more conductive wires electrically connected to the fifth conductive wire and the sixth conductive wire, which are disposed along a part of the boundary of an area in one or more additional planes parallel to and spaced apart from the third plane while being spaced apart from each other.

In the antenna device according to an embodiment, the conductive wires of the antenna device may be printed on a surface of a printed circuit board (PCB) having the shape of a cylinder.

In the antenna device according to an embodiment, a resonance frequency of the antenna device may vary in response to changes in the concentration of a target analyte around the antenna device.

The antenna device may further include a communication part for sending to an external device biological parameter data regarding variations of the resonance frequency of the antenna device and measured scattering parameters.

In the antenna device according to an embodiment, when a feed signal is fed to the antenna device, the first conductive wire capacitively couples with the third conductive wire, the third conductive wire capacitively couples with the fifth conductive wire, the second conductive wire capacitively couples with the fourth conductive wire, and the fourth conductive wire capacitively couples with the sixth conductive wire.

An antenna device according to another embodiment may include: first conductive wires disposed along a part of a first area in a first plane; second conductive wires which are disposed along a part of a second area in a second plane parallel to and spaced apart from the first plane, and which capacitively couple with the first conductive wires; and third conductive wires which are disposed along a part of a third area in a third plane parallel to and spaced apart from the second plane, and which capacitively couple with the second conductive wires, wherein the first conductive wires are connected to an antenna port and connected to the second conductive wires at a distal end relative to the antenna port, and the second conductive wires are connected to the third conductive wires at a proximal end relative to the antenna port, and a resonance generated by a magnetic dipole and a resonance generated by an electric dipole are formed separately in response to a feed signal fed to the antenna port.

An antenna device according to another embodiment may include: a first conductive wire which is disposed in a reference plane positioned halfway through a plurality of planes parallel to and spaced apart from each other, and which generates a resonance by a magnetic dipole; a second conductive wire which is disposed in one or more planes positioned on one side of the reference plane, and which generates a resonance by a first electric dipole in response; and a third conductive wire which is disposed in one or more planes positioned on the other side of the reference plane, and which generates a resonance by a second electric dipole of the opposite polarity to the first electric dipole.

BRIEF DESCRIPTION OF THE DRAWINGS

FIG. 5B explains the direction of current flowing through an antenna device according to an embodiment.

DETAILED DESCRIPTION OF THE INVENTION

Figure 1:
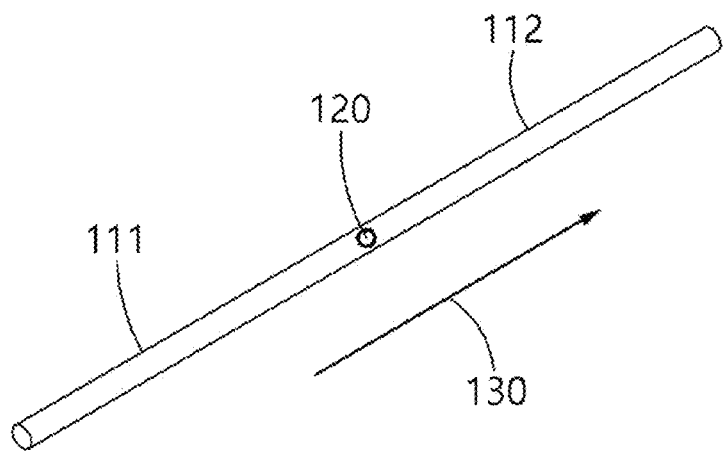
FIG. 1 shows a general shape of a dipole antenna.

Hereinafter, exemplary embodiments will be described in detail with reference to the accompanying drawings. However, since various changes may be made to the embodiments, the scope of the rights of the patent application is not limited or limited by these embodiments. It should be understood that all changes, equivalents, or substitutes to the embodiments are included in the scope of the rights.

The terms used in the example embodiments have been used for the purpose of explanation only, and the terms should not be interpreted as an intention of limiting the explanation. An expression of the singular number includes an expression of the plural number unless clearly defined otherwise in the context. In the present specification, it should be understood that a term such as "include" or "have" is used to specify existence of a feature, a number, a step, an operation, a constituent element, a part, or a combination thereof described in the specification, but it does not preclude the possibility of the existence or addition of one or more other features, numbers, steps, operations, constituent elements, parts, or combinations thereof.

Unless otherwise defined, all terms, including technical and scientific terms, used herein have the same meaning as commonly understood by one of ordinary skill in the art to which example embodiments pertain. Terms, such as those defined in commonly used dictionaries, should be interpreted as having meanings that are consistent with those in the context of the related art but are not interpreted as having ideal or excessively formal meanings unless clearly defined in the present application.

In addition, in the description with reference to the accompanying drawings, the same reference numerals are assigned to the same components regardless of the reference numerals, and redundant descriptions thereof will be omitted. In describing the embodiments, when it is determined that a detailed description of related known technologies may unnecessarily obscure the subject matter of the embodiments, the detailed description thereof will be omitted.

In describing the components of the embodiment according to the present invention, terms such as first, second, "A", "B", (a), (b), and the like may be used. These terms are merely intended to distinguish one component from another component, and the terms do not limit the nature, sequence or order of the components. When a component is described as "connected", "coupled", or "linked" to another component, this may mean the components are not only directly "connected", "coupled", or "linked", but also are indirectly "connected", "coupled", or "linked" via a third component.

A component that has the same common function as a component included in any one example embodiment will be described using the same name in other example embodiments. Unless otherwise stated, the description set forth in any one example embodiment may be applicable to other example embodiments, and a detailed description will be omitted in an overlapping range.

According to an embodiment, a technology regarding an in-body biosensor capable of semi-permanently measuring glucose is provided. The in-body biosensor may also be referred to as an invasive biosensor, an insertable biosensor, or an implantable biosensor. The in-body biosensor may be a sensor that senses a target analyte using electromagnetic waves. For example, the in-body biosensor may measure biometric information associated with a target analyte. Hereinafter, the target analyte is a material associated with a living body, and may also be referred to as a biological material (analyte). For reference, in the present specification, the target analyte has been mainly described as glucose, but is not limited thereto. The biometric information is information related to a biological component of a subject, and may include, for example, a concentration, level, etc., of an analyte. If the analyte is glucose, the biometric information may include a glucose level.

The in-body biosensor may measure biological parameters (hereinafter, referred to as "parameters") associated with the above-described biological component, and determine biometric information from the measured parameters. In the present specification, the parameters may represent circuit network parameters used to analyze a biosensor and/or a biosensing system. Hereinafter, for convenience of explanation, scattering parameters will be mainly described as an example, but the parameters set forth herein are not limited to them. As the parameters, for example, admittance parameters, impedance parameters, hybrid parameters, and transmission parameters may be used. For the scattering parameters, transmission coefficient and reflection coefficient may be used. For reference, the resonance frequency calculated from the above-described parameters may be related to the concentration of the target analyte, and the biosensor may predict glucose levels by detecting a change in the transmission coefficient and/or the reflection coefficient.

The in-body biosensor may include a resonator assembly (e.g., an antenna). Hereinafter, an example in which the resonator assembly is an antenna will be mainly described. The resonance frequency of the antenna may be expressed as a capacitance component and an inductance component as shown in Equation 1 below.

$$f = \frac{1}{2\pi\sqrt{LC}} \quad \text{[Equation 1]}$$

wherein f denotes the resonance frequency of an antenna included in the biosensor using electromagnetic waves, L denotes the inductance of the antenna, and C denotes the capacitance of the antenna. The capacitance C of the antenna may be proportional to a relative dielectric constant $\varepsilon_r$ as shown in Equation 2 below.

$$C \propto \varepsilon_r \quad \text{[Equation 2]}$$

The relative dielectric constant $\varepsilon_r$ of the antenna may be affected by the concentration of the target analyte around it. For example, when an electromagnetic wave passes through a material having a certain dielectric constant, changes in amplitude and phase may occur in the transmitted electromagnetic wave due to radio reflection and scattering. Since the degree of reflection and/or scattering of the electromagnetic wave varies depending on the concentration of the target analyte present around the biosensor, the relative dielectric constant $\varepsilon_r$ may also vary. This can be construed that a biological capacitance is formed between the biosensor and the target analyte, due to a fringing field generated by the electromagnetic wave radiated by the biosensor including an antenna. Since the relative dielectric constant $\varepsilon_r$ of the antenna varies with changes in the concentration of the target analyte, the resonance frequency of the antenna also varies. In other words, the concentration of the target analyte may correspond to the resonance frequency.

According to an embodiment, the in-body biosensor may radiate electromagnetic waves while sweeping the frequency and measure scattering parameters for the radiated electromagnetic waves. The in-body biosensor may determine a resonance frequency from the measured scattering parameters and estimate a glucose level corresponding to the determined resonance frequency. The in-body biosensor may be inserted into a subcutaneous layer and predict the level of glucose diffused from a blood vessel to interstitial fluid.

The in-body biosensor may estimate biometric information by identifying the amount of frequency transition in resonance frequency. For more accurate measurement of resonance frequency, a quality factor may be maximized. Hereinafter, an antenna structure with an improved quality factor in an antenna device used in a biosensor using electromagnetic waves will be described.

FIG. 1 shows a general shape of a dipole antenna.

A general dipole antenna 100 may include two straight conductive wires connected to a feeder 120. The two straight conductive wires may be connected via the feeder 120. A first conductive wire 111 and second conductive wire 112 of the dipole antenna may be connected to the feeder 120 in a straight shape, without facing each other. Here, the straight shape may refer to a shape in which the first conductive wire 111 and second conductive wire 112 of the dipole antenna 100 extend in opposite directions.

The feeder 120 may supply a feed signal to the dipole antenna via a port. The feed signal is a signal that is fed to the dipole antenna, which may be an oscillation signal that oscillates at a target frequency. The feeder 120 may supply a feed signal in such a way that the currents flow in the same direction through the first conductive wire 111 and second conductive wire 112 of the dipole antenna having a straight shape. For example, the current in the first conductive wire 111 of the dipole antenna may flow in a direction 130 at a certain time point, and the current in the second conductive wire 112 of the dipole antenna may flow in the same direction 130. Also, at another time point, currents may flow in opposite directions simultaneously through the first conductive wire 111 and second conductive wire 112 of the dipole antenna.

An electric dipole may be formed by the current flowing through the first conductive wire 111 of the dipole antenna 100, and an electric dipole may be likewise formed by the current flowing through the second conductive wire 112. Since the currents flowing through the first and second conductive wires of the dipole antenna go in the same direction, the directions of electric dipole moments of the electric dipoles formed by the first and second conductive wires may be the same.

Figure 2:
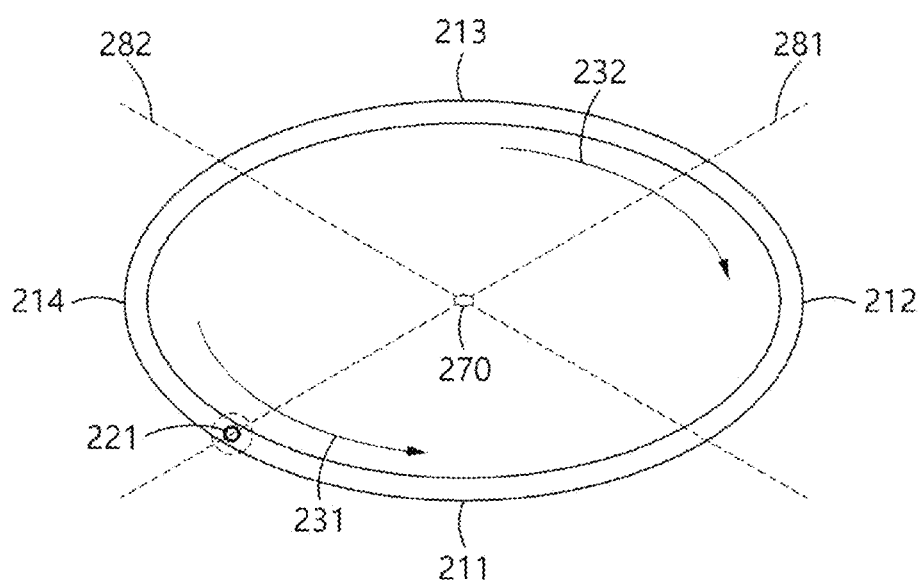
FIG. 2 shows an antenna element having a loop shape.

FIG. 2 shows an antenna element 200 having a loop shape.

The antenna element may have the shape of a closed loop. For example, as shown in FIG. 2, the antenna element 200 may include a first conductive wire 211, a second conductive wire 212, a third conductive wire 213, and a fourth conductive wire 214 that are connected together and have a circular shape. The first conductive wire 211 and the fourth conductive wire 214 may be disposed opposite each other with respect to a virtual straight line 281 passing through the center point 270 of a circle and an antenna port 221, and the second conductive wire 212 and the third conductive wire 213 may be disposed opposite each other with respect to the virtual straight line 281. Also, the first conductive wire 211 and the second conductive wire 212 may be disposed opposite each other with respect to a virtual straight line 282 passing through the center point 270 of the circle and orthogonal to the virtual straight line 281, and the third conductive wire 213 and the fourth conductive wire 214 may be disposed opposite each other with respect to the virtual straight line 282.

Moreover, the antenna element 200 may further include a feeder 221 for supplying a feed signal to an antenna via a port. The feeder 221 may be disposed between the first conductive wire 211 and the fourth conductive wire 214. Hereinafter, the direction of current flowing through each conductive wire when a feed signal is supplied to the antenna element 200 via the feeder 221 will be described.

For example, the length of the first conductive wire 211, second conductive wire 212, third conductive wire 213, and fourth conductive wire 214 of the antenna element 200 may have a length of ¼ of the wavelength of the frequency of the feed signal supplied from the feeder 221. While the feeder 221 is feeding a feed signal of a sinusoidal wave, the current flowing through a point corresponding to ¼ of the wavelength from the feeder 221 may have an intensity of 0 at a time point where the feeder 221 supplies a current with maximum intensity from the sinusoidal wave. At that time point, the current in the first conductive wire 211 may flow in a direction 231, and the current in the fourth conductive wire 214 may flow in the direction 231. At the same time, alternating current power is applied from the feeder 221, and the length of each conductive wire is ¼ of the wavelength corresponding to the power. Thus, the currents in the second conductive wire 213 and third conductive wire 213 may flow in a direction 232 which is the opposite direction of the direction 231. The direction 231 may be counterclockwise, and the direction 232 may be clockwise. As a result, it may be construed that, at that time point, an electric dipole is formed by the first conductive wire and the fourth conductive wire, and an electric dipole is formed by the second conductive wire and the third conductive wire.

Figure 3:
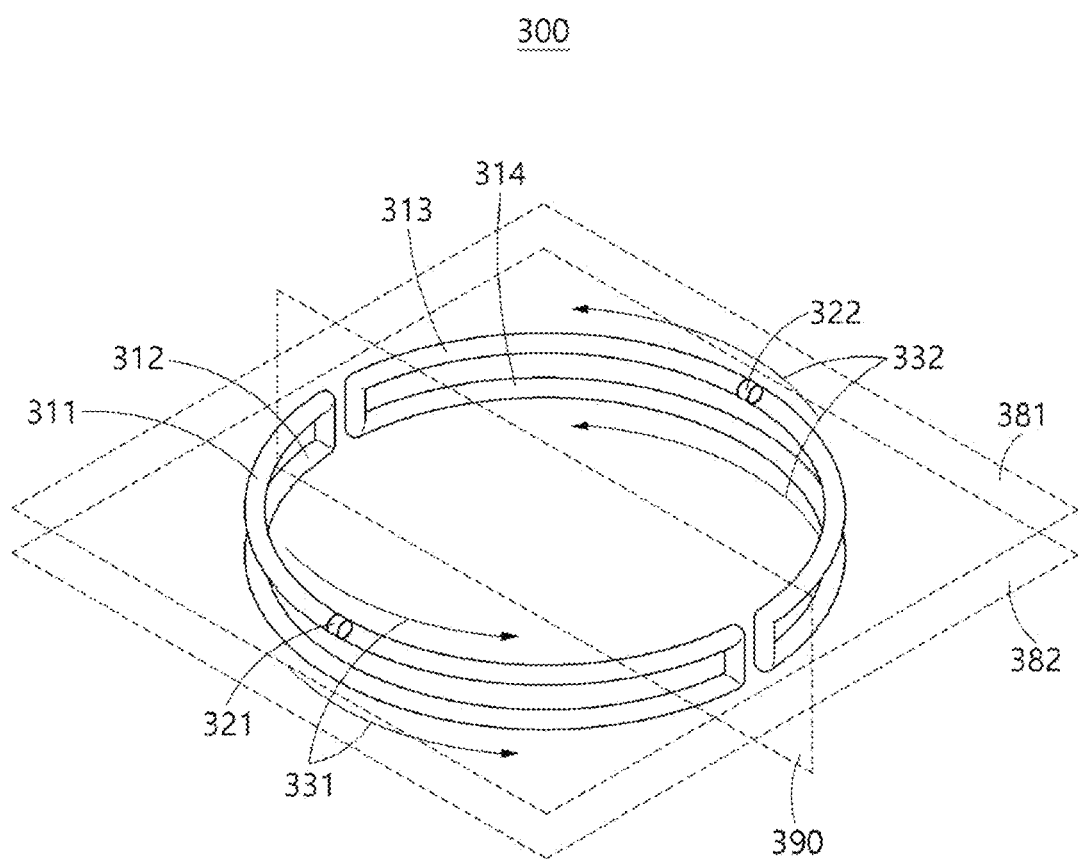
FIG. 3 shows an antenna element with two dipole antennas disposed adjacent to each other.

FIG. 3 shows an antenna element 300 with two dipole antennas disposed adjacent to each other.

The antenna device 300 may include a first dipole antenna and a second dipole antenna. The first dipole antenna may include a first conductive wire 311 and a second conductive wire 312. The second dipole antenna may include a third conductive wire 313 and the fourth conductive wire 314. The first conductive wire 311 of the first dipole antenna and the third conductive wire 313 of the second dipole antenna may be disposed in a first plane 381. The first conductive wire 311 and the third conductive wire 313 may be disposed opposite each other with respect to a virtual plane 390 perpendicular to the first plane 381. The virtual plane 390 may be disposed between the first dipole antenna and the second dipole antenna. Likewise, the second conductive wire 312 of the first dipole antenna and the fourth conductive wire 314 of the second dipole antenna may be disposed in a second plane 382. The second conductive wire 312 and the fourth conductive wire 314 may be disposed opposite each other with respect to the virtual plane 390.

The first dipole antenna and the second dipole antenna each may have a length equal to the wavelength of a target frequency. For example, FIG. 3 explains an example in which the closed loop is circular, and the first conductive wire 311 and the second conductive wire 312 each may have a length of half the wavelength of the target frequency. Similarly, the third conductive wire 313 and the fourth conductive wire 314 each may have a length of half the wavelength of the target frequency.

In this specification, the target frequency is a frequency at which the antenna device is desired to operate, for example, a frequency at which an antenna device inserted into the body is desired to resonate when the antenna device forms a biological capacitance for a target analyte with a given concentration inside the body.

The first dipole antenna may include a first feeder 321, and the second dipole antenna may include a second feeder 322. The first dipole antenna may have a folded shape by folding the antenna element having a closed-loop shape shown in FIG. 2 in half. Likewise, the second dipole antenna may have a folded shape as if by folding the antenna element having a closed-loop shape in half. For example, the first dipole antenna may have a folded shape as if by folding the antenna element at points on the conductive wires that are a ¼ wavelength away from the first feeder 321. The first conductive wire 311 and second conductive wire 312 of the first dipole antenna are disposed parallel to each other in a plane where they are spaced apart from each other, and may be connected through connection parts having via holes. For example, the first conductive wire 311 and the second conductive wire 312 may be symmetrical with respect to a virtual plane between the first plane 381 and the second plane 283, but are not limited to this. Likewise, the second dipole antenna may have a folded shape by folding the antenna element at points on the conductive wires that are a ¼ wavelength away from the second feeder 322.

The first feeder 321 may supply power to the first dipole antenna, and the second feeder 322 may supply power to the second dipole antenna. Hereinafter, the direction of current flowing through each conductive wire when a feed signal is supplied to the antenna element 300 via the feeders 321 and 322 will be described.

As explained above, it can be construed that, in the circular loop shown in FIG. 2, currents flow in opposite directions with respect to points on the conductive wires that are a ¼ wavelength away from the feeder 221, at a time point where the feeder 221 supplies a current with maximum intensity. Accordingly, in a case where the antenna element having a loop shape shown in FIG. 2 is folded as shown in FIG. 3, currents may flow in the same direction through the conductive wires in the antenna element having a folded loop shape, when viewed from a direction perpendicular to the first plane 381. For example, currents may flow through the first conductive wire 311 and second conductive wire 312 of the first dipole antenna in a first circulation direction 331 (e.g., counterclockwise in FIG. 3), and currents may flow through the third conductive wire 313 and fourth conductive wire 314 of the second dipole antenna in a second circulation direction 332 (e.g., counterclockwise) which is the same direction of circulation as the first circulation direction 331.

For reference, the direction of current circulation in this specification is a direction of current flowing through conductive wires disposed on a virtual closed loop and/or a part of the virtual closed loop, in a plane of the antenna element, which may refer to a direction in which current circulates clockwise or counterclockwise when viewed from a direction perpendicular to planes where the conductive wires are disposed. The clockwise or counterclockwise direction may be reversed depending on whether the planes are viewed from above or below and depending on the polarity of alternating current. For reference, the first circulation direction 331 and second circulation direction 332 of FIG. 3 may be clockwise at a time point where the feeders 321 and 322 feed a current with maximum intensity at which the polarity of the feed signal is positive.

In the first plane 381, currents flow in one direction through the first conductive wire 311 and third conductive wire 313 disposed corresponding in shape to a part of the closed loop, thereby forming a first magnetic dipole. Likewise, in the second plane 382, currents flow in one direction through the second conductive wire 312 and fourth conductive wire 314 disposed corresponding in shape to a part of the closed loop, thereby forming a second magnetic dipole. The directions of magnetic dipole moments of the first magnetic dipole and second magnetic dipole may be the same. Electromagnetic waves generated by the first magnetic dipole and electromagnetic waves generated by the second magnetic dipole may generate constructive interference.

A resonance generated by a magnetic dipole has a higher quality factor than a resonance generated by an electric dipole, and the quality factor may be expressed by the following equation:

$$Q(w) = \frac{1}{R}\sqrt{\frac{L}{C}} = \frac{1}{R_L + R_V}\sqrt{\frac{L}{C}}$$

wherein Q is quality factor, $R_L$ is the value of loss resistance, and $R_f$ is the value of radiation resistance.

Figure 4:
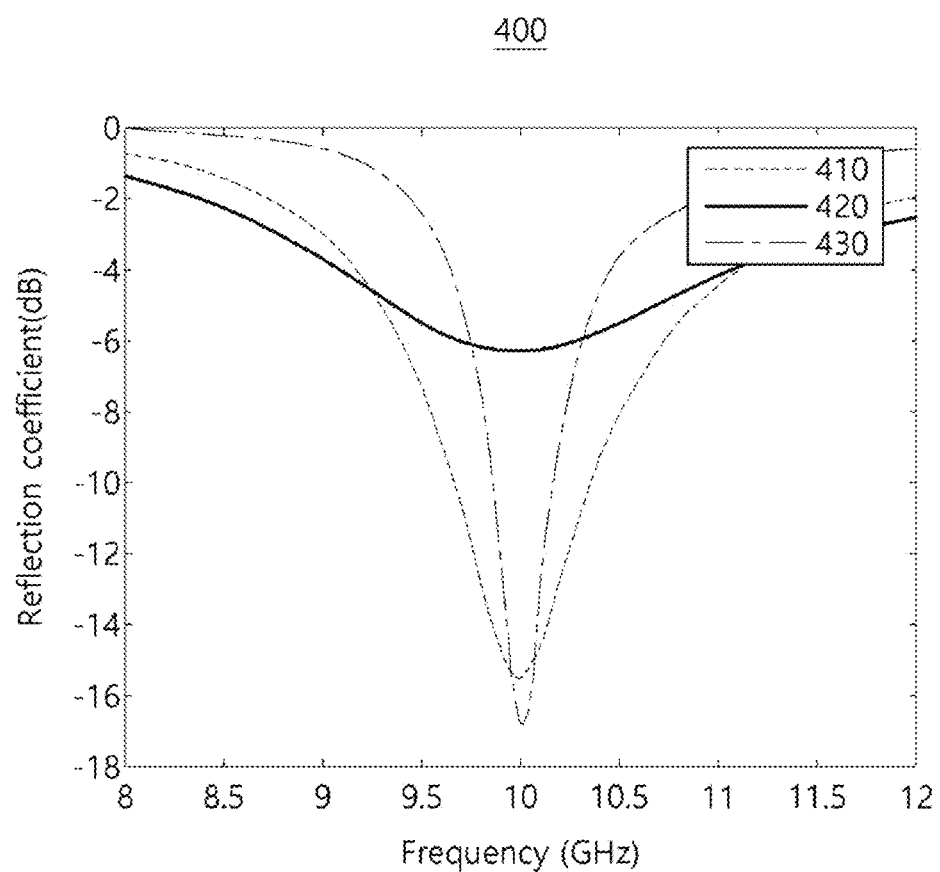
FIG. 4 shows frequency response characteristics for electromagnetic waves according to the type of the antenna element.

FIG. 4 shows frequency response characteristics for electromagnetic waves according to the type of the antenna element.

Frequency response characteristics 400 show frequency response characteristics for electromagnetic waves according to the type of the antenna element. A frequency response characteristic for scattered electromagnetic waves may be obtained by measuring parameters while sweeping the frequency. As shown in FIG. 4, the frequency response characteristic may be a reflection coefficient among scattering parameters.

A first reflection coefficient curve 410 represents a frequency response characteristic for the straight dipole antenna shown in FIG. 1. A second reflection coefficient curve 420 represents a frequency response characteristic for an antenna element having the shape of a closed loop shown in FIG. 2. A third reflection coefficient curve 430 represents a frequency response characteristic for the antenna element 300 forming a magnetic dipole shown in FIG. 3. The quality factor of the antenna element 300 forming a magnetic dipole may be relatively high.

Figure 5A:
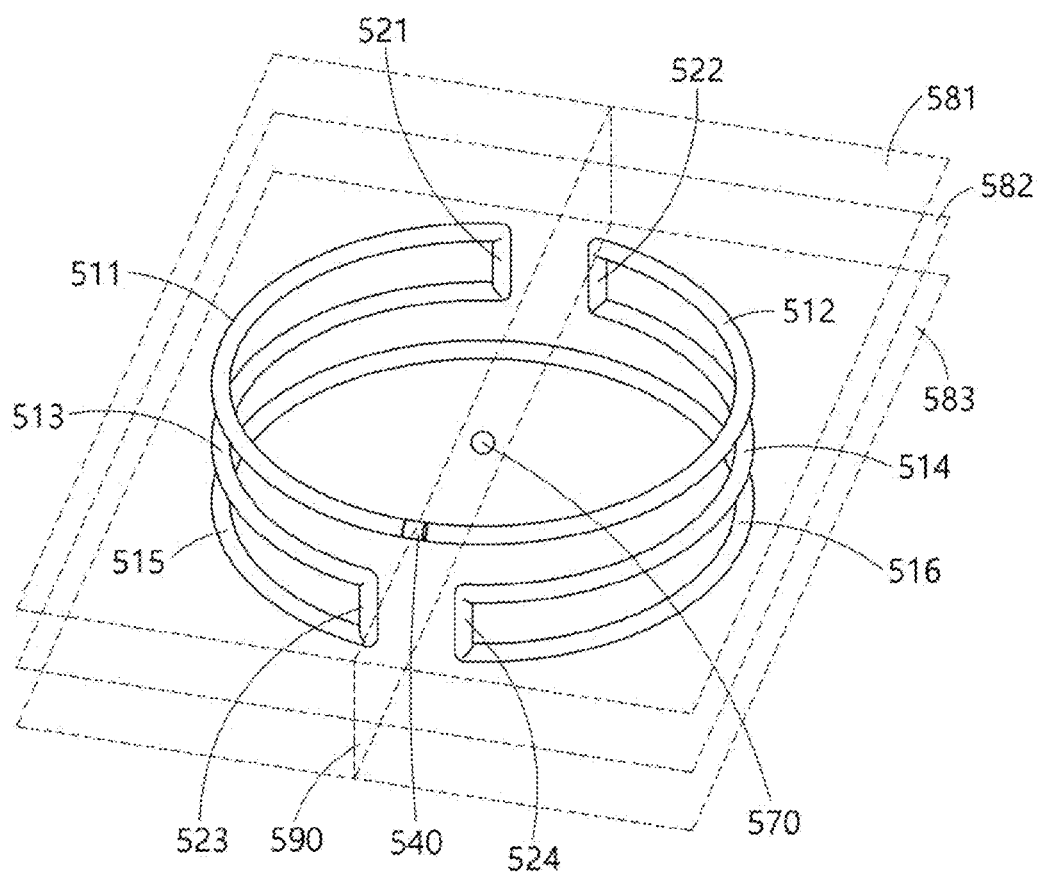
FIG. 5A explains the shape of an antenna device according to an embodiment.

FIG. 5A explains the shape of an antenna device 501 according to an embodiment.

The antenna device 501 according to an embodiment may be a conductive sensor. The antenna device 501 according to an embodiment may include: a first conductive wire 511 and a second conductive wire 512 which are disposed along a part of the boundary of a first area in a first plane 581 while being spaced apart from each other; a third conductive wire 513 and a fourth conductive wire 514 which are disposed along a part of the boundary of a second area in a second plane 582 parallel to and spaced apart from the first plane 581 while being spaced apart from each other; and a fifth conductive wire 515 and a sixth conductive wire 516 which are disposed along a part of the boundary of a third area in a third plane 583 parallel to and spaced apart from the second plane 582 while being spaced apart from each other. The antenna device 501 may include a first connection part 521 connecting a first end of the first conductive wire 511 to a first end of the third conductive wire 513; a second connection part 522 connecting a first end of the second conductive wire 512 to a first end of the fourth conductive wire 514; a third connection part 523 connecting a second end of the third conductive wire 513 to a second end of the fifth conductive wire 515; and a fourth connection part 524 connecting a second end of the fourth conductive wire 514 to a second end of the sixth conductive wire 516. In this case, the first end may represent a distal end relative to an antenna port, and the second end may represent a proximal end relative to the antenna port.

In the antenna device 501 according to an embodiment, the second end of the first conductive wire 511 and the second end of the second conductive wire 512 may be connected to an antenna port. The first conductive wire 511 and the second conductive wire 512 may be disposed opposite each other with respect to a virtual plane 590 passing through the antenna port and the center point 570 of the first area and perpendicular to the first plane 581. The third conductive wire 513 and the fourth conductive wire 514 may be disposed opposite each other with respect to the virtual plane 590, and the fifth conductive wire 515 and the sixth conductive wire 516 may be disposed opposite each other with respect to the virtual plane 590. The fifth conductive wire 515 and the sixth conductive wire 516 may be electrically connected to each other.

The antenna device 501 according to an embodiment may further include an antenna port to which the first conductive wire 511 and the second conductive wire 512 are connected and a feeder 540 for supplying a feed signal via the antenna port. The feeder 540 may cause a current to flow through each conductive wire by supplying power to the antenna device. When a feed signal is fed to the antenna device 501 according to an embodiment, the first conductive wire 511 may capacitively couple with the third conductive wire 513, the third conductive wire 513 may capacitively couple with the fifth conductive wire 515, the second conductive wire 512 may capacitively couple with the fourth conductive wire 514, and the fourth conductive wire 514 may capacitively couple with the sixth conductive wire 516.

To sum up, the antenna device 501 according to an embodiment may include a first conductive wire 511 and a second conductive wire 512 which are disposed along a part of a first area in the first plane 581, a third conductive wire 513 and a fourth conductive wire 514 which are disposed along a part of a second area in the second plane 582 parallel to and spaced apart from the first plane 581, and which capacitively couple with the first conductive wire 511 and the second conductive wire 512, and a fifth conductive wire 515 and a sixth conductive wire 516 which are disposed along a part of a third area in the third plane 583 parallel to and spaced apart from the second plane 582, and which capacitively couple with the third conductive wire 513 and the fourth conductive wire 514.

In the antenna device 501 according to an embodiment, a combination of one or two of the first conductive wire 511, the second conductive wire 512, the third conductive wire 513, the fourth conductive wire 514, the fifth conductive wire 515, and the sixth conductive wire 516 may have a length of ¼ of the wavelength of a target frequency. For example, the first conductive wire 511, the second conductive wire 512, the third conductive wire 513, the fourth conductive wire 514, the fifth conductive wire 515, and the sixth conductive wire 516 may have a length of ¼ of the wavelength.

Here, the wavelength of the target frequency may represent a guide wavelength. The relationship between the wavelength in air and the guide wavelength may be given by the following Equation 4.

$$\lambda_g = \frac{\lambda_0}{\sqrt{\varepsilon_r}} \quad [\text{Equation 4}]$$

wherein $\lambda_g$ is the guide wavelength, $\lambda_0$ is the wavelength in air, and $\varepsilon_r$ is the dielectric constant of a guide medium.

Since the antenna device 501 according to an embodiment forms capacitive coupling between the conductive wires, the wavelength of the target frequency may vary with the dielectric constant of a guide material. For example, since the length of each conductive wire of the antenna device 501 is ¼ of the wavelength of the target frequency, the length of the conductive wires of the antenna device may be decreased by increasing the dielectric constant of the guide medium.

In the antenna device 501 according to an embodiment, the first area, the second area, and the third area may be either polygonal or circular. For example, if the first area is circular as shown in FIG. 5A, the first conductive wire 511 and the second conductive wire 512 may be disposed corresponding in shape to a part of the circumference in the first plane 581. If the second area is circular, the third conductive wire 513 and the fourth conductive wire 514 may be disposed corresponding in shape to a part of the circumference in the second plane 582. If the third area is circular, the fifth conductive wire 515 and the sixth conductive wire 516 may be disposed corresponding in shape to a part of the circumference in the third plane 583. For another example, if the first area is polygonal unlike in FIG. 5A, the first conductive wire 511 and the second conductive wire 512 may be disposed corresponding in shape to a part of the polygon in the first plane 581. For example, the radius of the first area, second area, and third area may be, but not limited to, 2.4 mm, and the distance between the first area and the third area may be, but not limited to, 0.6 mm.

Furthermore, the first area, the second area, and the third area may have a closed loop shape, and the conductive wires may be disposed corresponding in shape to the areas.

In the antenna device 501 according to another embodiment, the first area, the second area, and the third area may be equal in size and shape when viewed from a direction perpendicular to the first plane 581.

The antenna device 501 according to one embodiment may supply power to the conductive wires by using one antenna port. The antenna device 501 may include conductive wires connected together by connection parts. Power may be supplied to the conductive wires by using one port. For example, an electrical path may be formed which sequentially connects the first conductive wire 511, third conductive wire 513, fifth conductive wire 515, sixth conductive wire 516, fourth conductive wire 514, and second conductive wire 512, from a first terminal of the antenna port to a second terminal of the antenna port.

For example, the first end of the first conductive wire 511 and the first end of the second conductive wire 512 may be disconnected from each other. The first conductive wire 511 may be connected to the first connection part 521, and the second conductive wire 512 may be connected to the second connection part 522. The first connection part 521 and the second connection part 522 may be disconnected from each other. Likewise, the third connection part 523 and the fourth connection part 524 may be disconnected from each other. A virtual straight line from the feeder 540 to the first connection part 521 may be at a threshold angle or lower with respect to the virtual plane 590. A virtual straight line from the feeder 540 to the second connection part 522 may be at a threshold angle or lower with respect to the virtual plane 590. The first connection part 521 and the second connection part 522 may be disposed symmetrically with respect to the virtual plane 590. For example, a virtual straight line from the feeder 540 to the first connection part 521 may be at an angle of 5 degrees with respect to the virtual plane 590, and a virtual straight line from the feeder 540 to the second connection part 522 may be at an angle of 5 degrees with respect to the virtual plane 590.

FIG. 5B explains the direction of current flowing through an antenna device according to an embodiment.

The first conductive wire 511, second conductive wire 512, third conductive wire 513, fourth conductive wire 514, fifth conductive wire 515, and sixth conductive wire 516 of the antenna device 502 shown in FIG. 5A may have a length of ¼ of the wavelength of a target frequency. The feeder 540 of the antenna device may supply power (e.g., a feed signal) to the antenna device 502. FIG. 5B shows that the conductive wires of the antenna device 502 shown in FIG. 5A are unfolded in a plane in order to interpret the direction of current. For reference, in this specification, it is construed that the direction of current and/or the direction of circulation is reversed if the current has opposite polarity.

FIG. 5B shows a current graph of a time point at which the intensity of current flow is zero at a point ⅛ wavelength away from the feeder 540. Hereinafter, the direction of current flowing through each conductive wire at that time point will be described. The current may flow clockwise in a conductive wire region from the feeder 540 to the point ⅛ wavelength away from it (hereinafter, '⅛ wavelength point'). It may be construed that, since the polarity of current is reversed at the ⅛ wavelength point, the direction of circulation is reversed too. The current may flow counterclockwise in a conductive wire region from the ⅛ wavelength point to a point ⅝ wavelength away from it (hereinafter, '⅝ wavelength point'). It may be construed that, since the polarity of current is reversed again at the ⅝ wavelength point, the direction of circulation is reversed again too. The current may flow clockwise in a conductive wire region from the ⅝ wavelength point to a point ¾ wavelength away from it (hereinafter, '¾ wavelength point').

Accordingly, since a current flows in one circulation direction (counterclockwise in FIG. 5B) in the second area defined by the third conductive wire 513 and the fourth conductive wire 514, a resonance generated by a magnetic dipole may be generated due to a circulating current flowing through the third conductive wire 513 and the fourth conductive wire 514. Also, since a current flows in a line of symmetry with respect to the ⅛ wavelength point in the first area defined by the first conductive wire 511 and the second conductive wire 512, the current may be construed as flowing in the same direction, i.e., a first linear direction (e.g., upward from below in FIG. 5B). In other words, the first conductive wire 511 and the second conductive wire 512 may operate as dipole antennas through which current flows in the first linear direction, and may generate a resonance by a first electric dipole. Similarly, since a current flows in a line-symmetric shape with respect to the ⅝ wavelength point, it may be construed that the current flows in a second linear direction (e.g., downward from above in FIG. 5B) opposite to the first linear direction. In other words, the fifth conductive wire 515 and the sixth conductive wire 516 may operate as dipole antennas through which current flows in a second linear direction, and may generate a resonance by a second electric dipole. The first electric dipole and the second electric dipole may have electric dipole moments of opposite polarities.

To sum up, in the antenna device according to an embodiment, conductive wires disposed in a reference plane positioned halfway through a plurality of planes parallel to and spaced apart from each other may generate a resonance by a magnetic dipole, in response to a feed signal. In the antenna device according to an embodiment, conductive wires disposed in one or more planes positioned on one side of the reference plane may generate a resonance by a first electric dipole in response to the feed signal, and conductive wires disposed in one or more planes positioned on the other side of the reference plane may generate a resonance by a second electric dipole of the opposite polarity to the first electric dipole in response to the feed signal.

As shown in FIG. 5A, the first electric dipole formed by the conductive wires in the first plane and the second electric dipole formed by the conductive wires in the third plane have opposite polarities, and therefore the resonances generated by the electric dipoles in the first and third planes may cancel out each other in the conductive wires in the second plane between the first and third planes. As the intensity of sinusoidal waves changes over time, the conductive wires in the reference plane may repeatedly show an increase and decrease in the strength of the magnetic dipole formed by the current flowing in the first circulation direction and an increase and decrease in the strength of the magnetic dipole formed by the current flowing in the second circulation direction. The conductive wires in the other planes may repeatedly show an increase and decrease in the strength of the electric dipole formed by the current flowing in the first linear direction and the second linear direction. In this case, electric dipoles of opposite polarities may be formed in planes positioned on opposite sides of the reference plane.

Accordingly, the antenna device 501 may form two resonances separately by the first electric dipole and the second electric dipole, along with a resonance generated by a magnetic dipole with a high equality factor, in response to a feed signal fed to the antenna port. The antenna device 501 may show at least three resonance frequencies.

Figure 6:
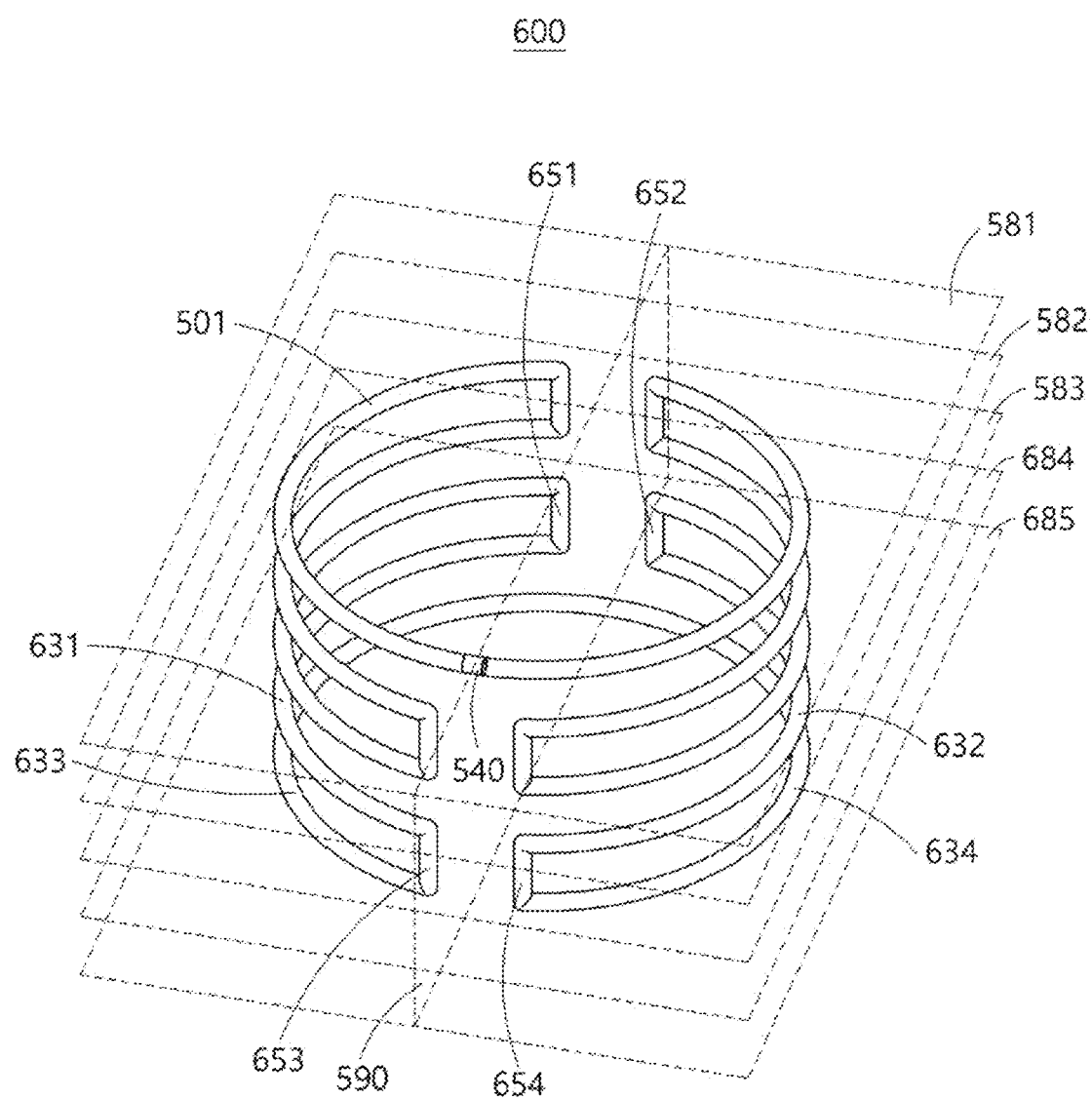
FIG. 6 explains the shape of an antenna device according to an embodiment.

FIG. 6 explains the shape of an antenna device according to an embodiment.

According to an embodiment, the fifth conductive wire and the sixth conductive wire may be electrically connected to each other. For example, the first end of the fifth conductive wire of the antenna device and the first end of the sixth conductive wire may be connected together. In the above, FIG. 5A explains an example in which the fifth end of the fifth conductive wire of the antenna device and the first end of the sixth conductive wire are physically and directly connected, and FIG. 6 explains an example in which they are indirectly connected via an additional conductive wire.

For example, an antenna device 600 may further include an additional conductive wire in addition to the antenna device 501 of FIG. 5A. The antenna device 600 may further include a seventh conductive wire 631 and an eighth conductive wire 632 which are disposed along a part of the boundary of a fourth area in a fourth plane 684 parallel to and spaced apart from the third plane while being spaced apart from each other, and a ninth conductive wire 633 and a tenth conductive wire 634 which are disposed along a part of the boundary of a fifth area in a fifth plane 685 parallel to and spaced apart from the fourth plane while being spaced apart from each other. Further, the antenna device 600 according to an embodiment may further include a fifth connection part 651 connecting a first end of the fifth conductive wire to a first end of the seventh conductive wire; a sixth connection part 652 connecting a first end of the sixth conductive wire 653 to a first end of the eighth conductive wire 632; a seventh connection part 653 connecting a second end of the seventh conductive wire 631 to a second end of the ninth conductive wire 633; and an eighth connection part 654 connecting a second end of the eighth conductive wire 632 to a second end of the tenth conductive wire 634.

However, the antenna device according to an embodiment is not limited to this but may further include conductive wires which are disposed along a part of the boundary of an area in one or more additional planes parallel to and spaced apart from the third plane while being spaced apart from each other, as is the case for the antenna device 600. For example, the antenna device may include conductive wires disposed in (2n+1) planes parallel to and spaced apart from each other, in order to form a resonance frequency by a magnetic dipole. Here, n may denote a natural number equal to or greater than 1. In this case, the length of the conductive wires may be, but not limited to, ¼ of the wavelength. The length of the conductive wires may be slightly different from ¼ of the wavelength.

Figure 7:
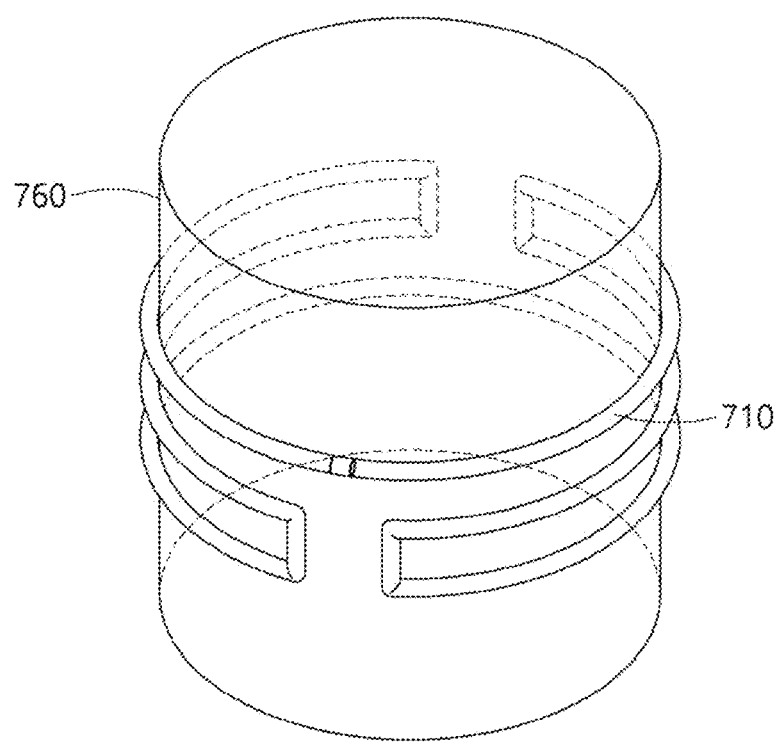
FIG. 7 shows a cylindrical sensor including an antenna device according to an embodiment.

FIG. 7 shows a cylindrical sensor including an antenna device according to an embodiment.

The cylindrical sensor 700 may be a sensor that has an antenna device 710 according to an embodiment printed on a surface of a printed circuit board (PCB) 760 having the shape of the side of a cylinder. For example, the antenna device 710 may be the antenna device shown in FIG. 5A. For example, the printed circuit board 760 may have the shape of a hollow cylinder. The conductive wires and connection parts of the antenna device 710 may be printed on the printed circuit board. The connection parts may be comprised of conductive wires as well. For another example, the cylindrical sensor 700 may be fabricated by printing the conductive wires and connection parts of the antenna element on a flat flexible printed circuit board (FPCB) and rolling the antenna element into a cylindrical shape so that the terminals of the antenna port are disposed adjacent to each other.

Figure 8:
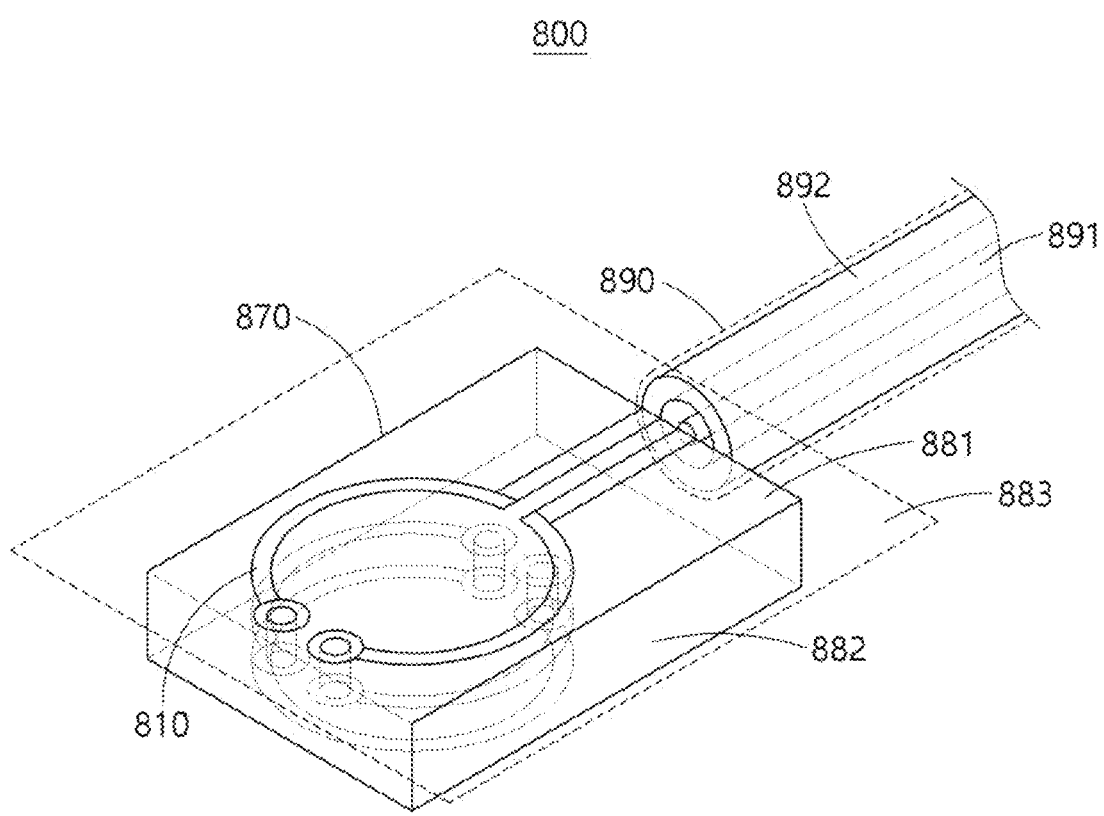
FIG. 8 shows a PCB-type sensor including an antenna device according to an embodiment of the present disclosure.

FIG. 8 shows a PCB-type sensor including an antenna device according to an embodiment of the present disclosure.

FIG. 8 shows a PCB-type sensor 800 that has an antenna device 810 according to an embodiment printed on a multilayered printed circuit board (PCB) 870. For example, the antenna device 810 may be the antenna device shown in FIG. 5.

The first conductive wire and second conductive wire of the antenna device may be disposed on a first side 881 of the printed circuit board 870, and the fifth conductive wire and the sixth conductive wire may be disposed on a second side 882 opposite to the first side 881. Also, the third conductive wire and the fourth conductive wire may be disposed on a third side 883 between the first side 881 and the second side 882. Each side may be made of a layer. The first connection part, second connection part, third connection part, and fourth connection part of the antenna device 810 may connect between the conductive wires through via holes.

The first conductive wire and second conductive wire of the antenna device 810 according to an embodiment may be connected to the antenna port. The antenna port may be connected to a coaxial cable 890. The coaxial cable 890 may include an inner conductor 891 and an outer conductor 892. For example, the inner conductor 891 may be connected to the second end of the first conductive wire of the antenna device 810, and the outer conductor 892 may be connected to the second end of the second conductive wire of the antenna device 810. The coaxial cable may supply power to the antenna device 810 using the inner conductor 891 and the outer conductor 892. For example, the second end of the first conductive wire may be an input port of the antenna port, and the second end of the second conductive wire may be an output port of the antenna port.

Figure 9A:
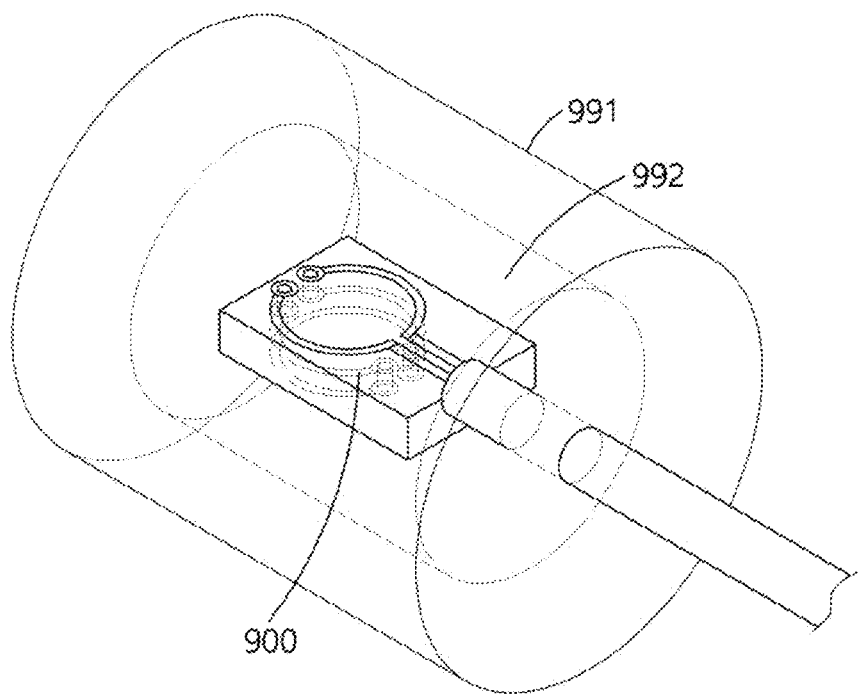
FIGS. 9A and 9B show the shape of an in-body biosensor including an antenna device according to an embodiment.
Figure 9B:
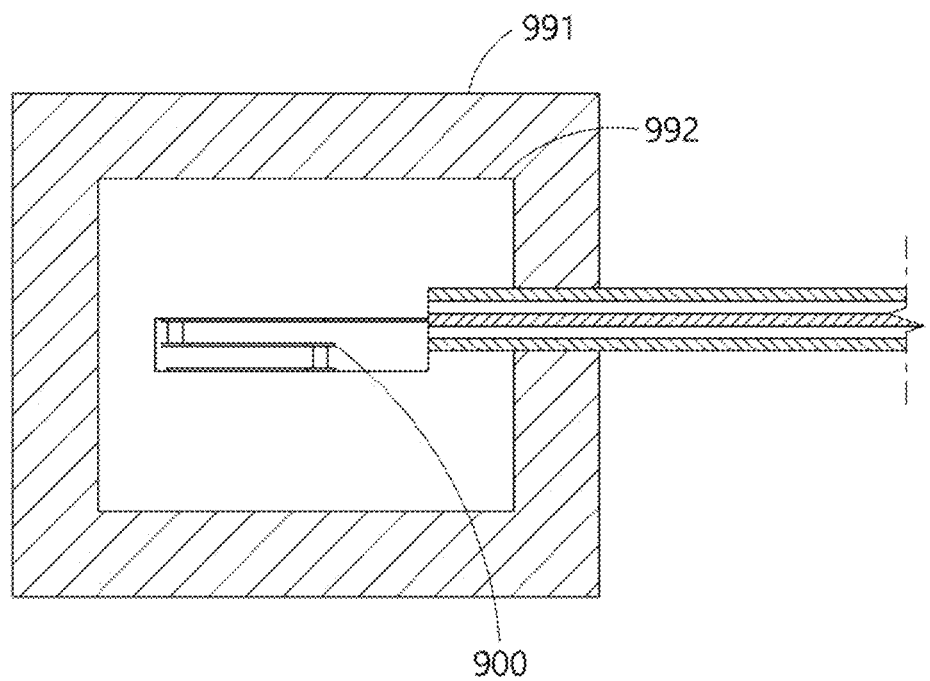

FIGS. 9A and 9B show the shape of an in-body biosensor including an antenna device according to an embodiment.

FIG. 9A may show a perspective view of the sensor according to an embodiment. FIG. 9B may show a front view of the sensor according to an embodiment.

A PCB-type sensor 900 including an antenna device according to an embodiment may sense a target analyte by using electromagnetic waves in the body. FIGS. 9A and 9B show a testing device 901 that holds water around the PCB-type sensor 900 in order to conduct testing. In the testing device 901, the PCB-type sensor 800 of FIG. 8 may be contained in a cylindrical inner space 992. A cylindrical space 991 having a larger diameter than the cylindrical inner space 992 may surround the cylindrical inner space 992. In the testing device 901, a change in dielectric constant caused by a temperature change may be observed.

Figure 10A:
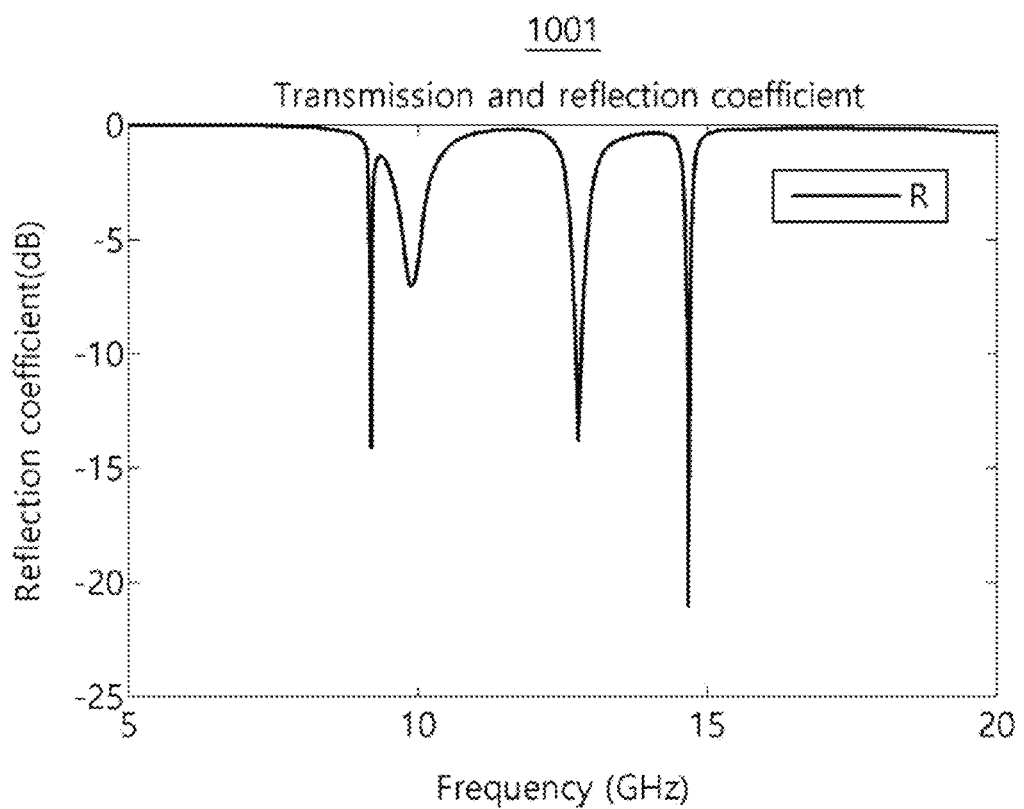
FIGS. 10A to 10O show frequency response characteristics for electromagnetic waves according to the type of the sensor.
Figure 10C:
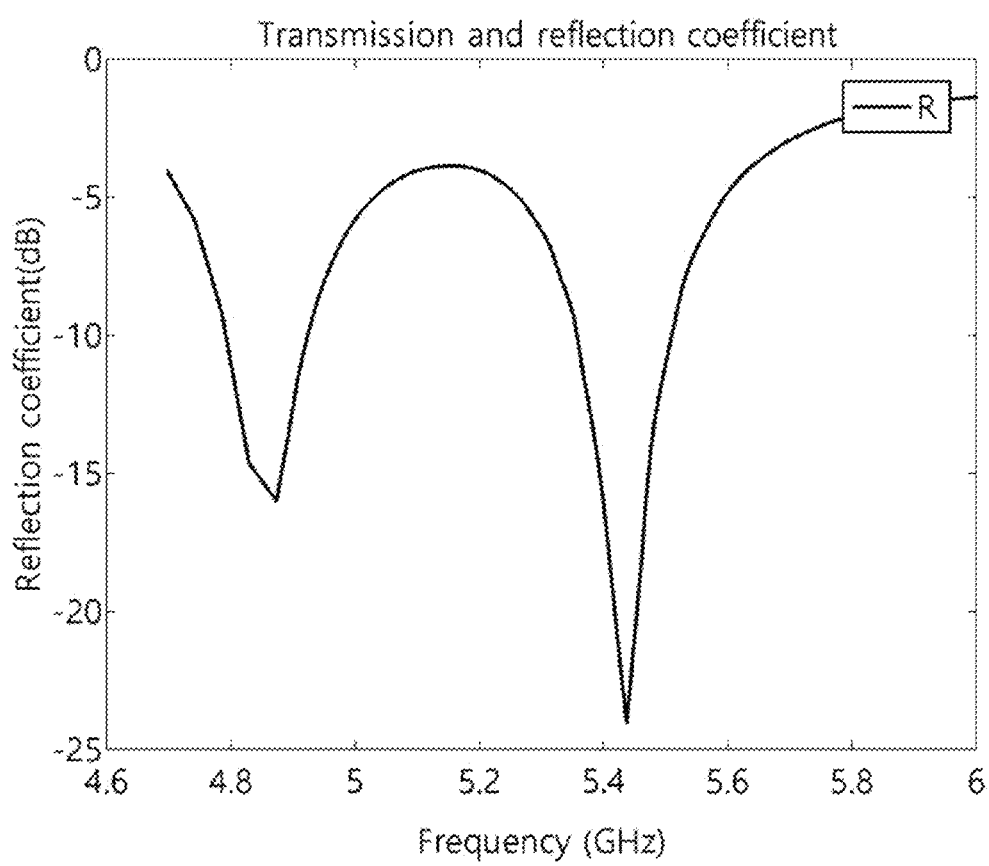

FIGS. 10A to 10O show frequency response characteristics for electromagnetic waves according to the type of the sensor.

A frequency response characteristic for a scattered electromagnetic field may be obtained by measuring parameters while sweeping the frequency. The frequency response characteristic may be a reflection coefficient among scattering parameters. A frequency response characteristic 1001 of FIG. 10A may represent a frequency response characteristic for electromagnetic waves obtained by the conductive wire-type sensor 501. A frequency response characteristic 1002 of FIG. 10B may represent a frequency response characteristic for electromagnetic waves obtained by the PCB-type sensor 800. A frequency response characteristic 1003 of FIG. 10O may represent a frequency response characteristic for electromagnetic waves obtained by the sensor 901 of FIG. 9A. A resonance frequency may be obtained by a frequency response characteristic, and the resonance frequency may refer to a frequency that exhibits a lower reflection coefficient than frequencies around it.

Figure 11A:
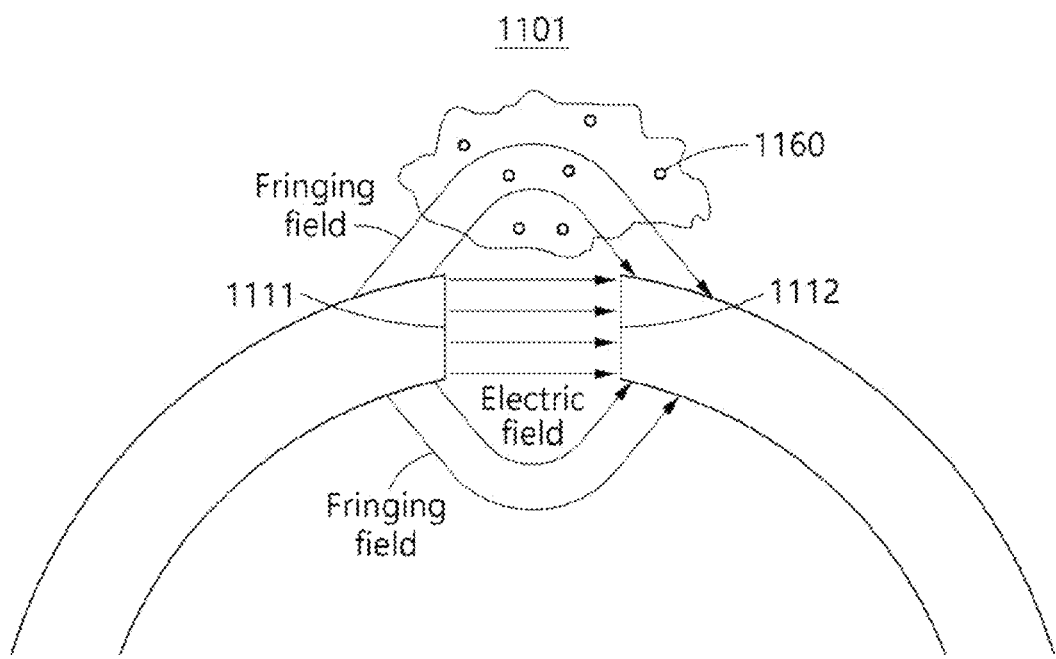
FIG. 11A explains how the resonance frequency of an antenna device according to an embodiment varies with the concentration of a target analyte around the antenna device.

FIG. 11A explains how the resonance frequency of an antenna device according to an embodiment varies with the concentration of a target analyte around the antenna device.

The antenna device according to an embodiment may include conductive wires 1111 and 1112 spaced apart from each other. For example, the conductive wire 1111 may correspond to the first connection part 521 of the antenna device 501 shown in FIG. 5A, and the conductive wire 1112 may correspond to the second connection part 522. However, this is merely an example given for convenience of explanation, and other connection parts spaced apart from each other may be described in a similar way.

For example, a strong electric field may be generated between the conductive wire 1111 and the conductive wire 1112. In other words, capacitive coupling may be formed between the conductive wire 1111 and the conductive wire 1112. On the contrary, a fringing field with a relatively low electric field intensity may be formed in a three-dimensional space around the conductive wire 1111 and the conductive wire 1112. If a target analyte is located in the fringing field around the antenna device, a biological capacitance between the sensor and the target analyte may change. As a result, the relative dielectric constant $\varepsilon_r$ of the antenna varies with changes in the concentration of the target analyte around the antenna, and the resonance frequency of the antenna also may vary. Accordingly, it is possible to calculate the concentration of the target analyte by measuring the variation in the resonance frequency of the antenna.

Figure 11B:
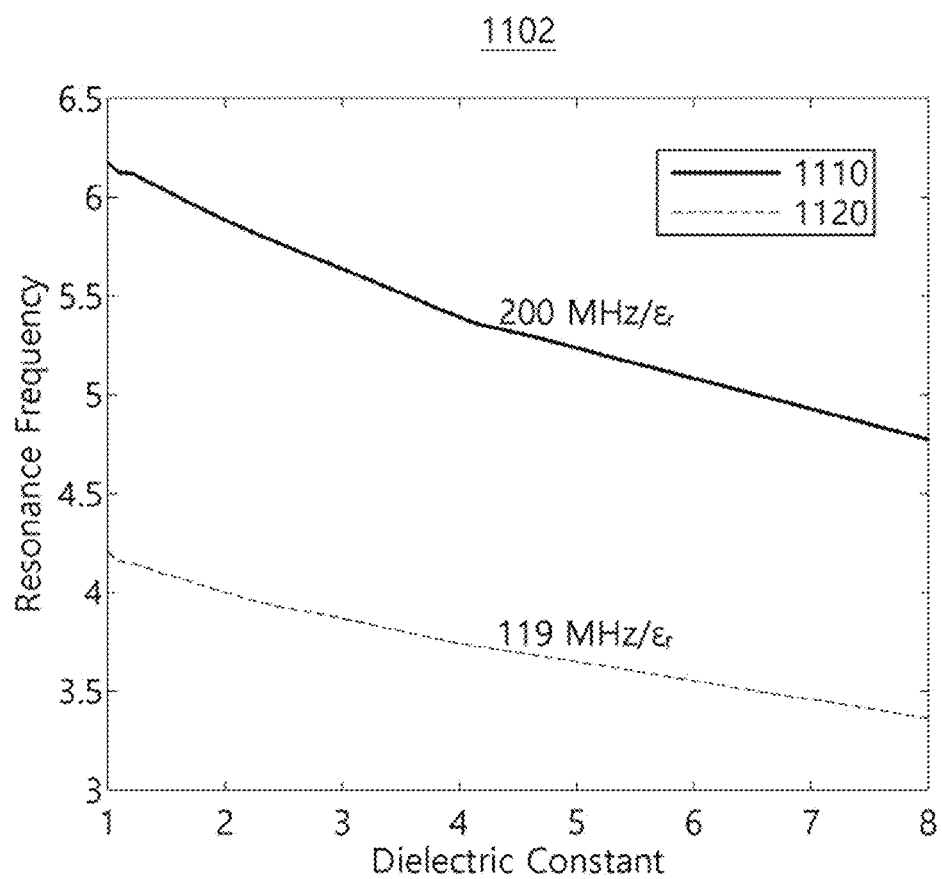
FIG. 11B shows how resonance frequency varies with relative dielectric constant.

FIG. 11B shows how resonance frequency varies with relative dielectric constant.

A graph 1110 represents a resonance frequency generated by a magnetic dipole. In the graph 1110, the resonance frequency may decrease as the relative dielectric constant of the target analyte around the antenna device increases. A graph 1120 represents a resonance frequency generated by an electric dipole. In the graph 1120, the resonance frequency may decrease as the relative dielectric constant of the target analyte around the antenna device increases. However, the amount of transition in the resonance frequency generated by the magnetic dipole and the amount of transition in the resonance frequency generated by the electric dipole become different as the relative dielectric constant increases. For example, the difference in resonance frequency between the magnetic dipole and the electric dipole decreases as the relative dielectric constant of the target analyte increases.

Figure 12A:
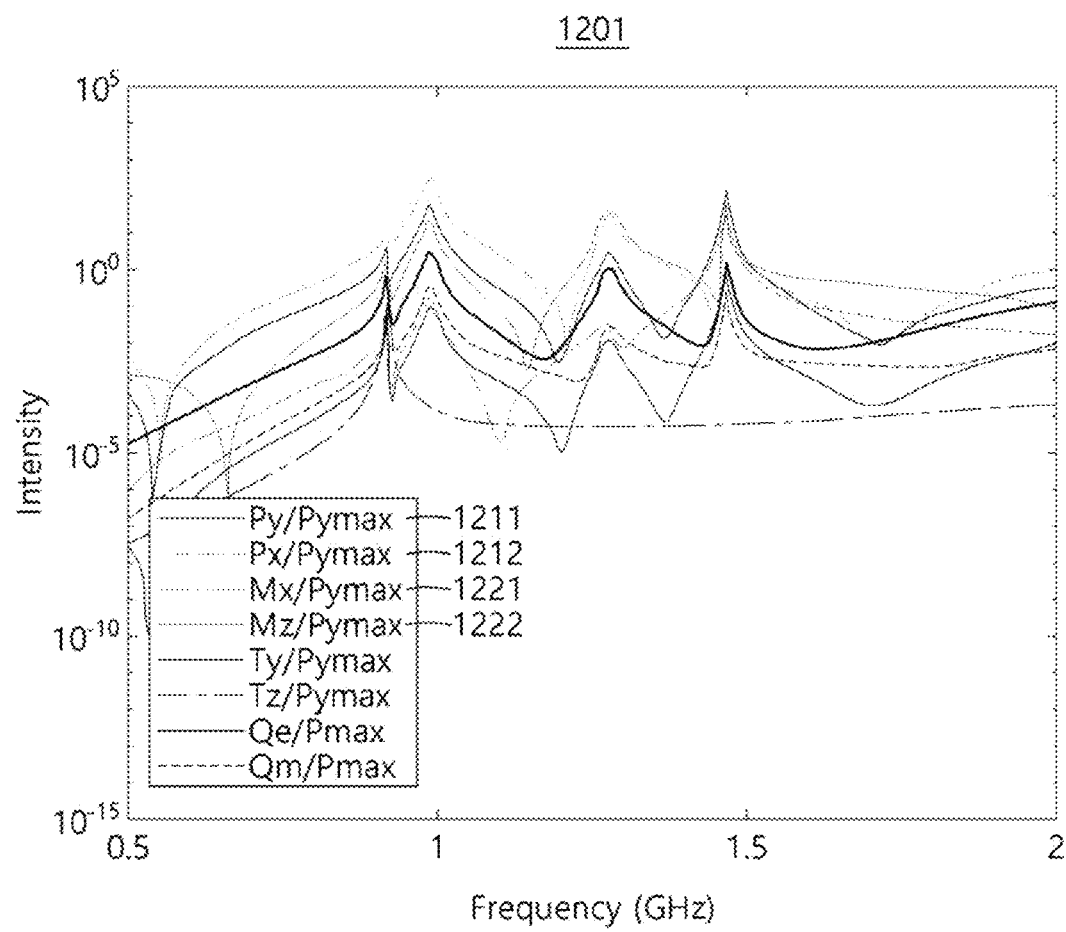
FIGS. 12A to 12C show frequency response characteristics for a magnetic dipole and an electric dipole.
Figure 12B:
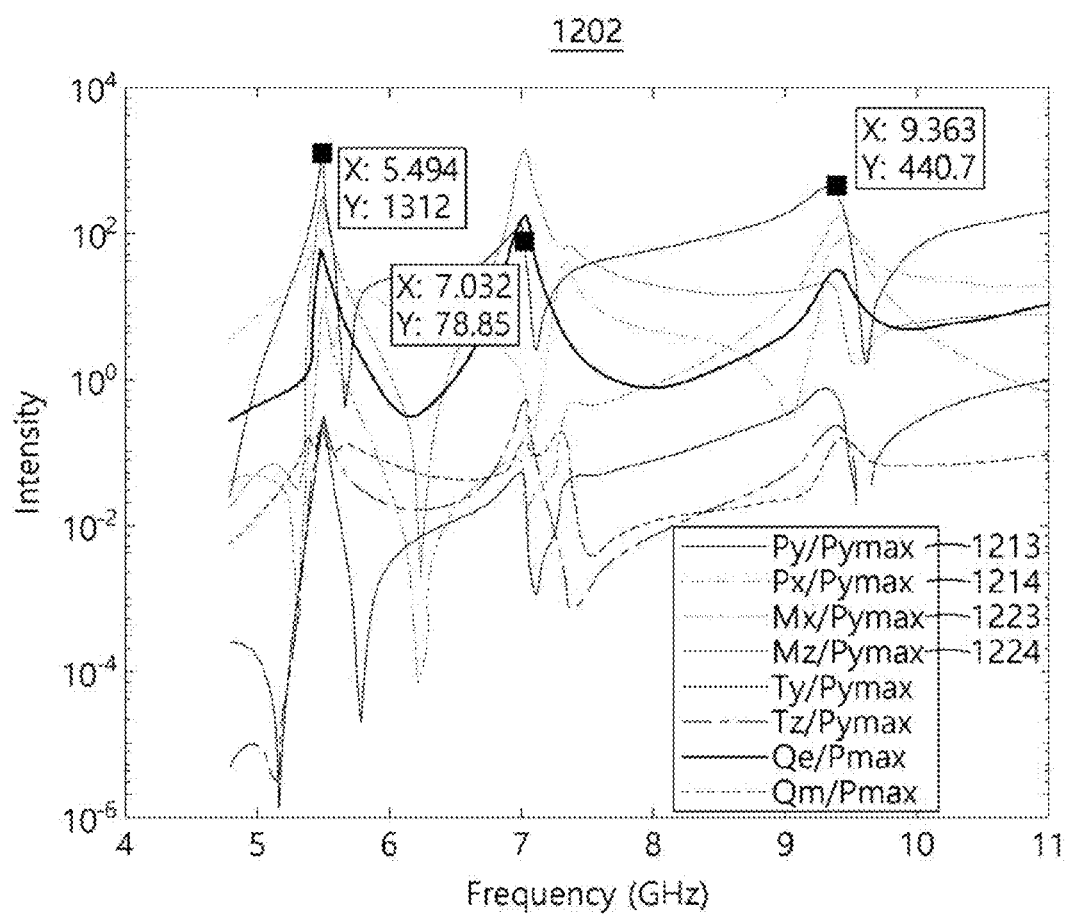
Figure 12C:
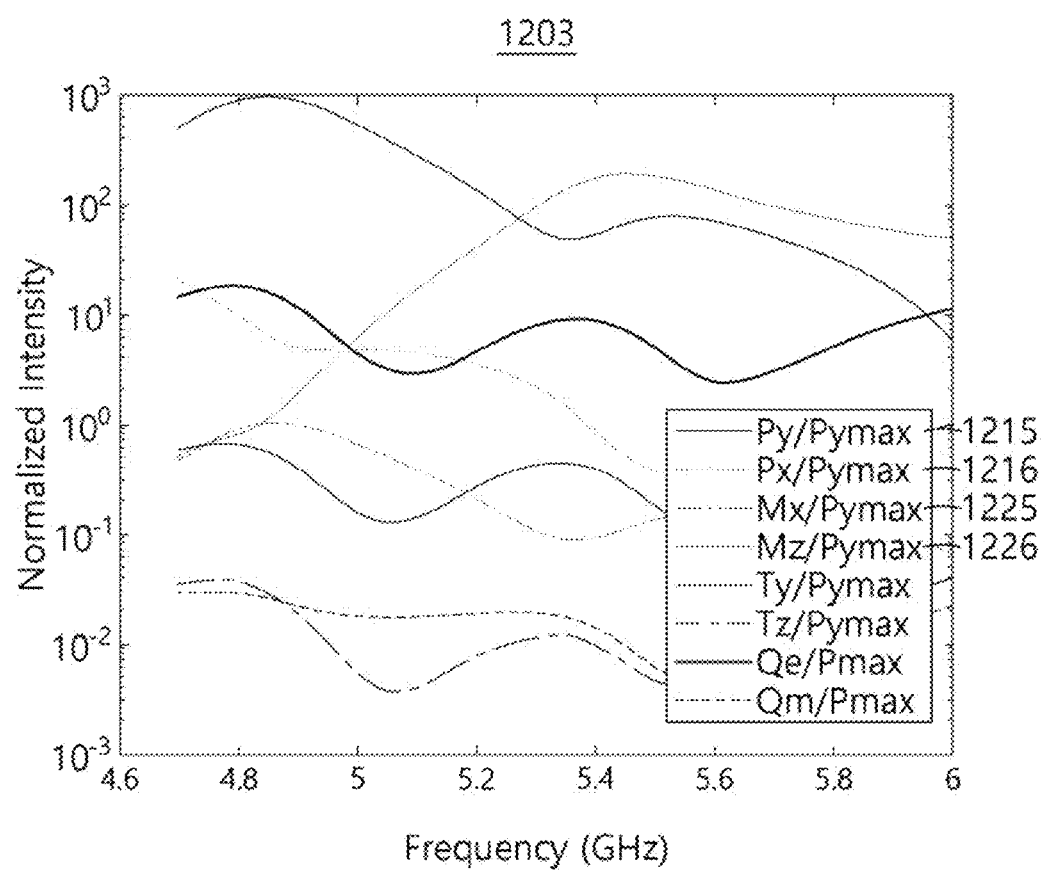

FIGS. 12A to 12C show frequency response characteristics for a magnetic dipole and an electric dipole.

A sensor including an antenna device according to an embodiment may generate resonances separately for a magnetic dipole and an electric dipole. FIGS. 12A to 12C show frequency response characteristics according to the shape of the sensor. A frequency response characteristic for each dipole may be obtained by measuring each dipole's moment while sweeping the frequency. The frequency response characteristic may represent the intensity of the moment. Frequency response characteristics 1201 of FIG. 12A may represent frequency response characteristics for a dipole for the conductive wire-type sensor 501. A graph 1211 and a graph 1212 may represent frequency response characteristics for an electric dipole, and a graph 1221 and a graph 1222 may represent frequency response characteristics for a magnetic dipole. Frequency response characteristics 1202 of FIG. 12B may represent frequency response characteristics for a dipole for the PCB-type sensor 800. A graph 1213 and a graph 1214 may represent frequency response characteristics for an electric dipole, and a graph 1223 and a graph 1224 may represent frequency response characteristics for a magnetic dipole. Frequency response characteristics 1203 of FIG. 12C may represent frequency response characteristics for a dipole for the sensor 901 of FIG. 9A. A graph 1215 and a graph 1216 may represent frequency response characteristics for an electric dipole, and a graph 1225 and a graph 1226 may represent frequency response characteristics for a magnetic dipole.

Figure 13:
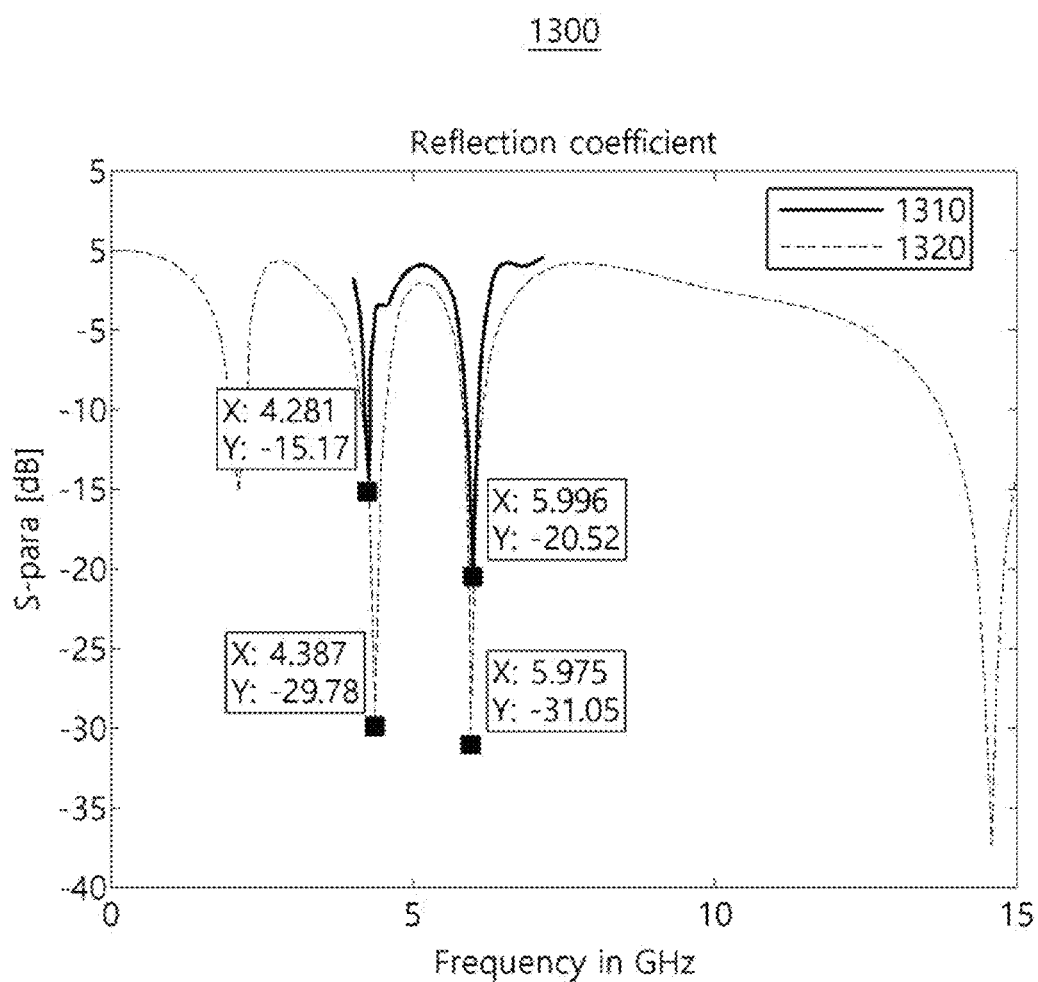
FIG. 13 shows frequency response characteristics for electromagnetic waves.

FIG. 13 shows frequency response characteristics for electromagnetic waves.

Frequency response characteristics 1300 may represent frequency response characteristics for electromagnetic waves of an antenna device. A frequency response characteristic for scattered electromagnetic waves may be obtained by measuring parameters while sweeping the frequency. As shown in FIG. 13, the frequency response characteristic may be a reflection coefficient among scattering parameters. A first reflection coefficient curve 1310 may represent a frequency response characteristic measured by the PCB-type sensor 800. For example, a resonance frequency may be generated at 4.387 GHz and 5.975 GHz on the first reflection coefficient curve 1310. A second reflection coefficient curve 1320 may represent a frequency response characteristic measured via simulation. For example, a resonance frequency may be generated at 4.281 GHz and 5.996 GHz on the second reflection coefficient curve 1320.

Figure 14:
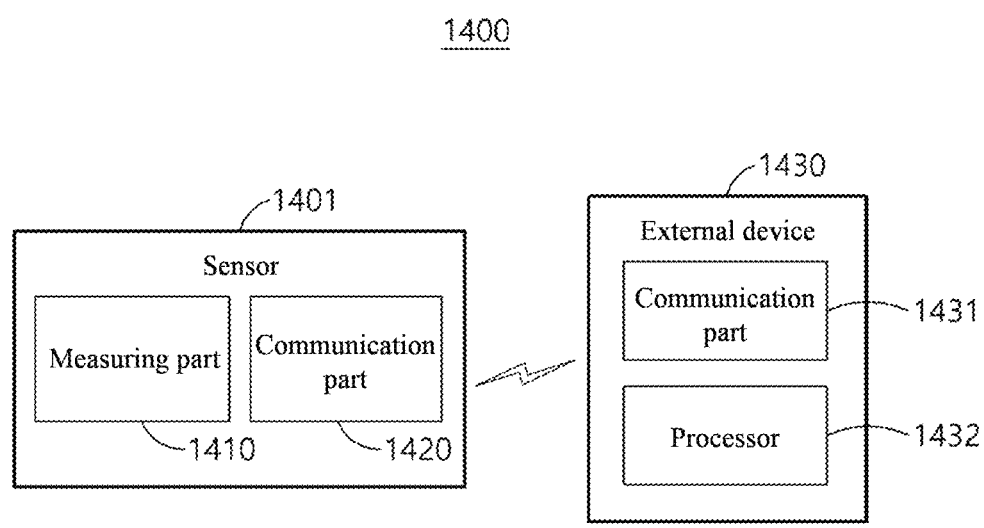
FIG. 14 is a block diagram showing a glucose measurement system according to an embodiment.

FIG. 14 is a block diagram showing a glucose measurement system according to an embodiment.

The glucose measurement system 1400 according to an embodiment may include an in-body biosensor 1401 and an external device 1430. The in-body biosensor 1401 may include a measuring part 1410 and a communication part 1420.

For example, the in-body biosensor 1401 shown in FIG. 14 may be placed subcutaneously into a subject, and the external device 1430 may be placed outside the body of the subject.

The measuring part 1410 is an antenna element, which may include a resonator assembly, for example, a resonant element. The antenna element and/or the resonator assembly may have a structure of the antenna device shown in FIG. 7. The measuring part 1410 of the in-body biosensor 1401 may measure biological parameters for the antenna device. The in-body biosensor 1401 placed subcutaneously into the subject may generate a signal by sweeping the frequency within a preset frequency band and feed the generated signal to the resonant element. The sensor 1401 may measure scattering parameters for the resonant element to which a signal with varying frequency is supplied.

The communication part 1420 may send to the external device 1430 data indicating the measured scattering parameters. Also, the communication part 1420 may receive power for generating a signal supplied to the measuring part 1410 by using a wireless power transmission method. The communication part 1420 may include a coil to wirelessly receive power or send data.

The external device 1430 may include a communication part 1431 and a processor 1432. The communication part 1431 of the external device 1430 may receive biological parameters from a glucose measurement device that measures the biological parameters which change with biometric information associated with a target analyte. For example, the communication part 1431 may receive biological parameter data (e.g., scattering parameters and variations in resonance frequency) of the resonant element measured by the measuring part 1410. The processor 1432 of the external device 1430 may determine biometric information (e.g., glucose levels) by using the received biological parameter data. The external device 1430 may also be referred to as a biometric information processing device. A biometric information processing device that determines information indicating glucose levels as biometric information may be referred to as a glucose determination device. For example, the processor 1432 of the external device 1430 may determine glucose levels for a living body by using biological parameter data.

As explained above, the antenna element may represent three or more resonance frequencies generated by an electric dipole and a magnetic dipole. Accordingly, the glucose measurement system 1400 may determine biometric information (e.g., glucose levels and variations in glucose levels) by tracking changes in each of the three or more resonance frequencies. For example, the values of the three or more resonance frequencies may be mapped to each glucose level. For example, a look-up table in which resonance frequencies of 1 GHz, 1.25 GHz, and 1.5 GHz are mapped to a glucose level XX mg/dL may be stored. The glucose measurement system 1400 may search the look-up table for glucose levels that match measured resonance frequencies. However, the determination of glucose levels is not limited to the above method, but a variety of methods may be used according to design.

Moreover, an example in which the in-body biosensor 1401 transmits biological parameters to the external device 1430 without processing them has been mainly described, but the present disclosure is not limited to this. For example, the in-body biosensor 1401 may further include its own processor, and the processor of the in-body biosensor 1401 may determine glucose levels. In this case, the sensor 1401 may transmit the determined glucose levels to the external device via a communication part. Also, an additional device (not shown) including a processor may be placed subcutaneously and establish human body communication with the in-body biosensor 1401. In this case, the additional device (not shown) may receive measured biological parameter data directly from the in-body biosensor 1401 to determine glucose levels. Also, the additional device (not shown) may send the determined glucose levels to the external device 1430 from inside the body of the subject.

Although the above-mentioned embodiments have been described by limited drawings, those skilled in the art may apply various technical modifications and alterations based on the above embodiments. For example, appropriate results can be achieved although described techniques are carried out in a different order from a described method, and/or described elements are combined or mixed in a different form from the described method, or replaced or substituted with other elements or equivalents.

Therefore, other implementations, other embodiments, and equivalents to patent claims belong to the scope of the patent claims to be described later.

What is claimed is:

1. An antenna device comprising:
   a first conductive wire and a second conductive wire which are disposed along a part of the boundary of a first area in a first plane while being spaced apart from each other;
   a third conductive wire and a fourth conductive wire which are disposed along a part of the boundary of a second area in a second plane parallel to and spaced apart from the first plane while being spaced apart from each other;
   a fifth conductive wire and a sixth conductive wire which are disposed along a part of the boundary of a third area in a third plane parallel to and spaced apart from the second plane while being spaced apart from each other;
   a first connection part connecting a first end of the first conductive wire to a first end of the third conductive wire;

a second connection part connecting a first end of the second conductive wire to a first end of the fourth conductive wire;

a third connection part connecting a second end of the third conductive wire to a second end of the fifth conductive wire; and a fourth connection part connecting a second end of the fourth conductive wire to a second end of the sixth conductive wire.

2. The antenna device of claim 1, wherein the second end of the first conductive wire and the second end of the second conductive wire are connected to an antenna port, the first conductive wire and the second conductive wire are disposed opposite each other with respect to a virtual plane passing through the antenna port and the center point of the first area and perpendicular to the first plane, the third conductive wire and the fourth conductive wire are disposed opposite each other with respect to the virtual plane, and the fifth conductive wire and the sixth conductive wire are disposed opposite each other with respect to the virtual plane.

3. The antenna device of claim 1, further comprising:
an antenna port to which the first conductive wire and the second conductive wire are connected; and
a feeder for supplying a feed signal via the antenna port.

4. The antenna device of claim 3, wherein a virtual straight line from the feeder to the first connection part is at a threshold angle or lower with respect to the virtual plane, and a virtual straight line from the feeder to the second connection part is at a threshold angle or lower with respect to the virtual plane.

5. The antenna device of claim 1, wherein a combination of one or two of the first conductive wire, the second conductive wire, the third conductive wire, the fourth conductive wire, the fifth conductive wire, and the sixth conductive wire has a length of ¼ of the wavelength of a target frequency.

6. The antenna device of claim 1, wherein the first area, the second area, and the third area are either polygonal or circular.

7. The antenna device of claim 1, wherein the first area, the second area, and the third area are equal in size and shape when viewed from a direction perpendicular to the first plane.

8. The antenna device of claim 1, wherein the first connection part and the second connection part are disconnected from each other, and the third connection part and the fourth connection part are disconnected from each other.

9. The antenna device of claim 1, wherein conductive wires disposed in a reference plane positioned halfway through a plurality of planes parallel to and spaced apart from each other generate a resonance by a magnetic dipole, in response to a feed signal.

10. The antenna device of claim 9, wherein conductive wires disposed in one or more planes positioned on one side of the reference plane generate a resonance by a first electric dipole in response to the feed signal, and conductive wires disposed in one or more planes positioned on the other side of the reference plane generate a resonance by a second electric dipole of the opposite polarity to the first electric dipole in response to the feed signal.

11. The antenna device of claim 1, wherein the connection parts connect between the conductive wires through via holes.

12. The antenna device of claim 1, wherein the fifth conductive wire and the sixth conductive wire are electrically connected to each other.

13. The antenna device of claim 1, further including one or more conductive wires electrically connected to the fifth conductive wire and the sixth conductive wire, which are disposed along a part of the boundary of an area in one or more additional planes parallel to and spaced apart from the third plane while being spaced apart from each other.

14. The antenna device of claim 1, wherein the conductive wires of the antenna device are printed on a surface of a printed circuit board (PCB) having the shape of a cylinder.

15. The antenna device of claim 1, wherein a resonance frequency of the antenna device varies in response to changes in the concentration of a target analyte around the antenna device.

16. The antenna device of claim 1, further comprising a communication part for sending to an external device biological parameter data regarding variations of the resonance frequency of the antenna device and measured scattering parameters.

17. The antenna device of claim 1, wherein, when a feed signal is fed to the antenna device, the first conductive wire capacitively couples with the third conductive wire, the third conductive wire capacitively couples with the fifth conductive wire, the second conductive wire capacitively couples with the fourth conductive wire, and the fourth conductive wire capacitively couples with the sixth conductive wire.

18. An antenna device comprising:
first conductive wires disposed along a part of a first area in a first plane;
second conductive wires which are disposed along a part of a second area in a second plane parallel to and spaced apart from the first plane, and which capacitively couple with the first conductive wires; and
third conductive wires which are disposed along a part of a third area in a third plane parallel to and spaced apart from the second plane, and which capacitively couple with the second conductive wires,
wherein the first conductive wires are connected to an antenna port and connected to the second conductive wires at a distal end relative to the antenna port, and the second conductive wires are connected to the third conductive wires at a proximal end relative to the antenna port, and a resonance generated by a magnetic dipole and a resonance generated by an electric dipole are formed separately in response to a feed signal fed to the antenna port.

* * * * *